United States Patent [19]

Green

[11] 4,204,623

[45] May 27, 1980

[54] MANUALLY POWERED SURGICAL STAPLING INSTRUMENT

[75] Inventor: David T. Green, Norwalk, Conn.

[73] Assignee: United States Surgical Corporation, Norwalk, Conn.

[21] Appl. No.: 925,170

[22] Filed: Jul. 17, 1978

[51] Int. Cl.² .............................................. B25C 5/10
[52] U.S. Cl. .................................... 227/19; 227/121; 227/129; 227/138
[58] Field of Search ................. 227/19, 121, 129, 135, 227/138

[56] References Cited

U.S. PATENT DOCUMENTS

| Re. 28,932 | 8/1976 | Noiles et al. | 227/19 |
|---|---|---|---|
| 2,042,958 | 6/1936 | Pankonin | 227/121 |
| 2,874,384 | 2/1959 | Krone | 227/19 |
| 3,618,842 | 11/1971 | Bryan | 227/19 |
| 3,638,847 | 2/1972 | Noiles et al. | 227/19 |
| 3,643,851 | 2/1972 | Green et al. | 227/19 |
| 3,717,294 | 2/1973 | Green | 227/19 |
| 3,775,826 | 12/1973 | Reed | 29/212 D |
| 3,819,100 | 6/1974 | Noiles et al. | 227/19 |
| 3,837,555 | 9/1974 | Green | 227/19 |
| 3,873,016 | 3/1975 | Fishbein | 227/19 |
| 3,949,924 | 4/1976 | Green | 227/132 |
| 4,109,844 | 8/1978 | Becht | 227/19 |

*Primary Examiner*—John McQuade
*Attorney, Agent, or Firm*—Fleit & Jacobson

[57] ABSTRACT

A manually powered surgical stapling instrument for applying sterilized staples to the disunited skin or fascia of a patient for effecting a joining of the skin or fascia. The instrument is adapted to associate with a staple carrying cartridge having an anvil at one end thereof and adapted to house a plurality of staples therein. A pusher element slidably mounted in the cartridge is provided for advancing the staples in the cartridge, for ejecting the staples from the cartridge and for forming the staples around the anvil. The surgical stapling instrument comprises a main body portion adapted for mounting the staple carrying cartridge, a thrust bar mounted to reciprocate in the main body portion for driving the pusher element forward to advance, eject and form the staples, a handle arrangement for receiving a manually applied force, and a linkage arrangement for directly transmitting the manually applied force to the thrust bar to advance the thrust bar and thereby advance, eject and form the staples.

52 Claims, 43 Drawing Figures

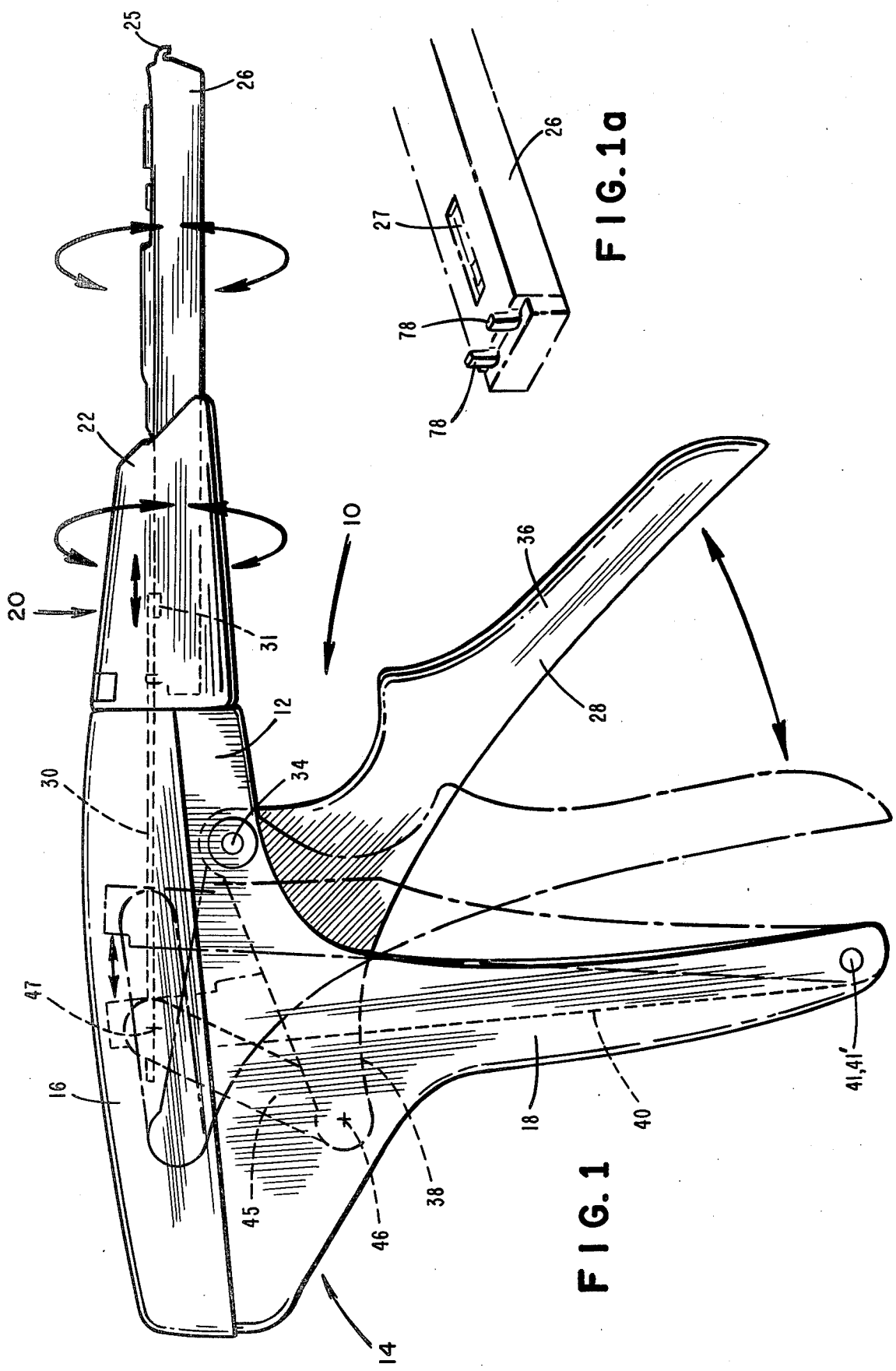

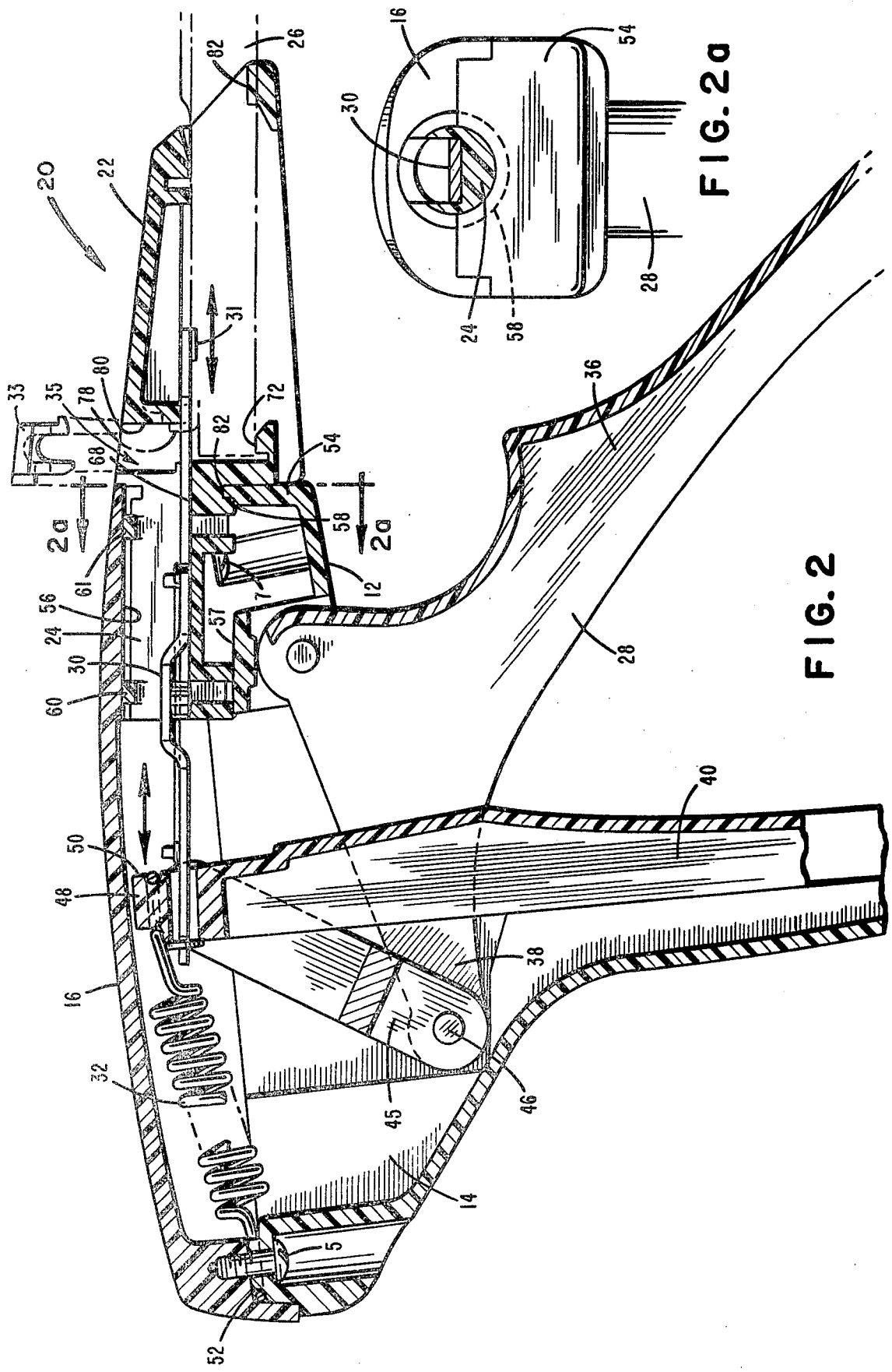

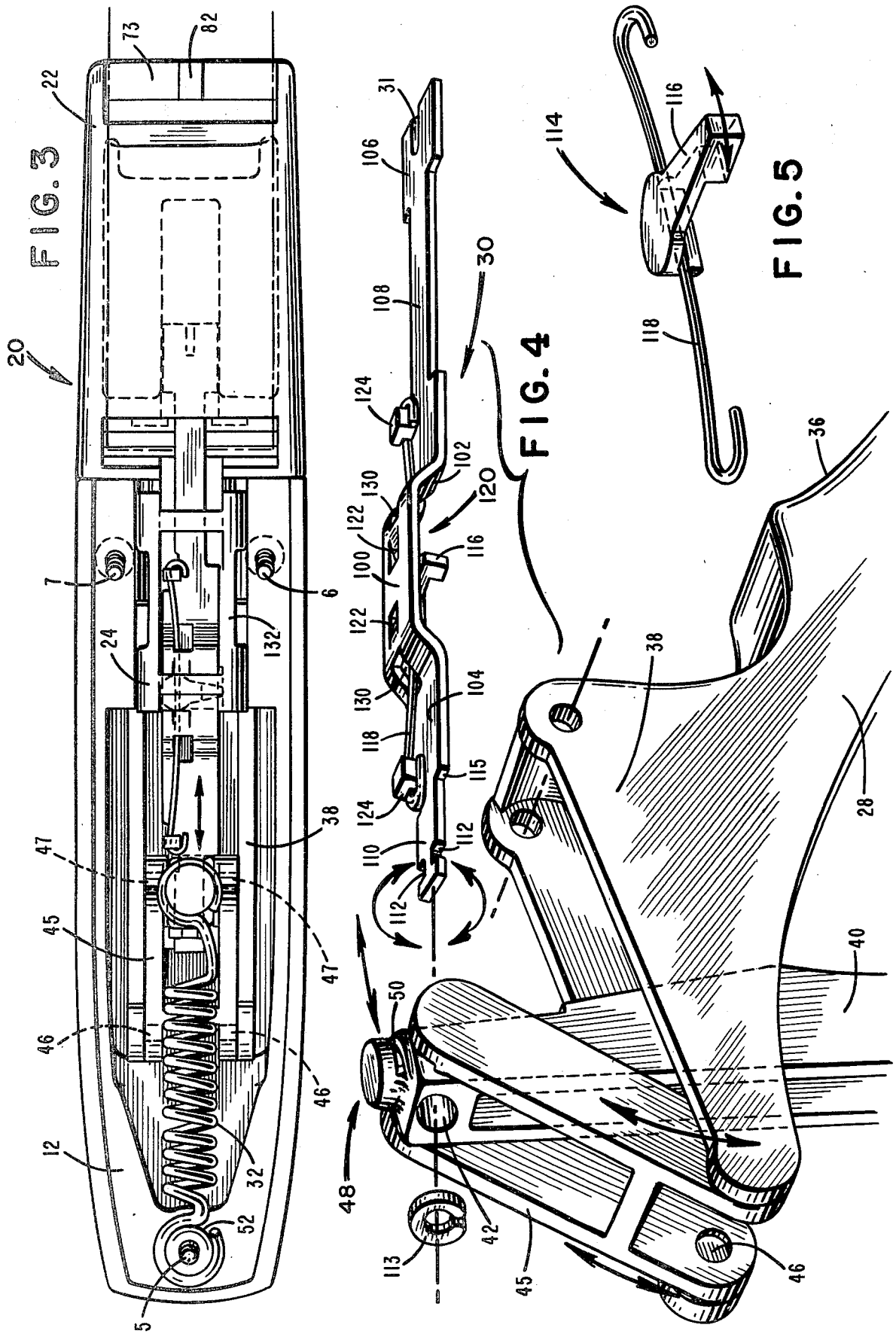

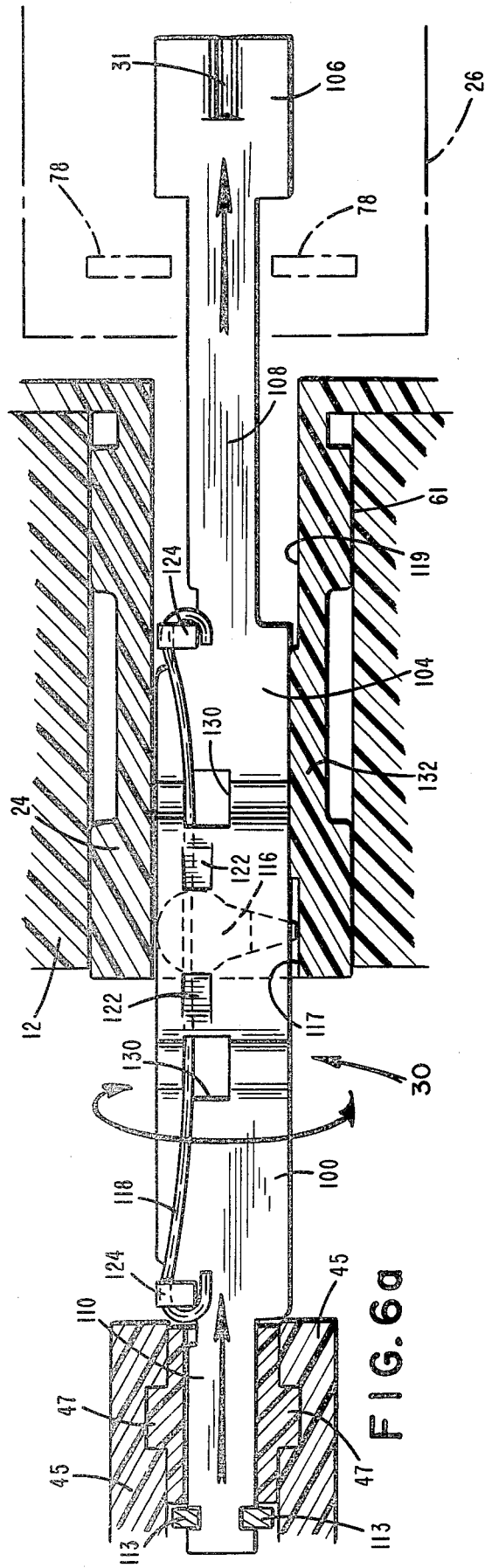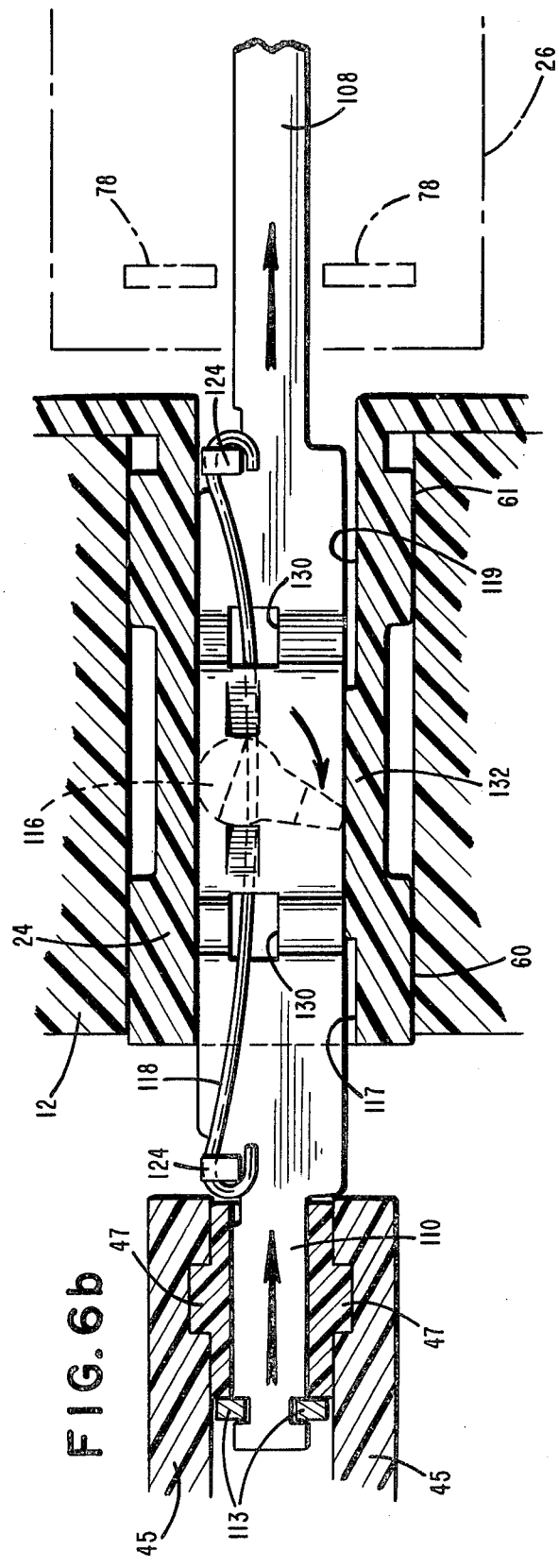

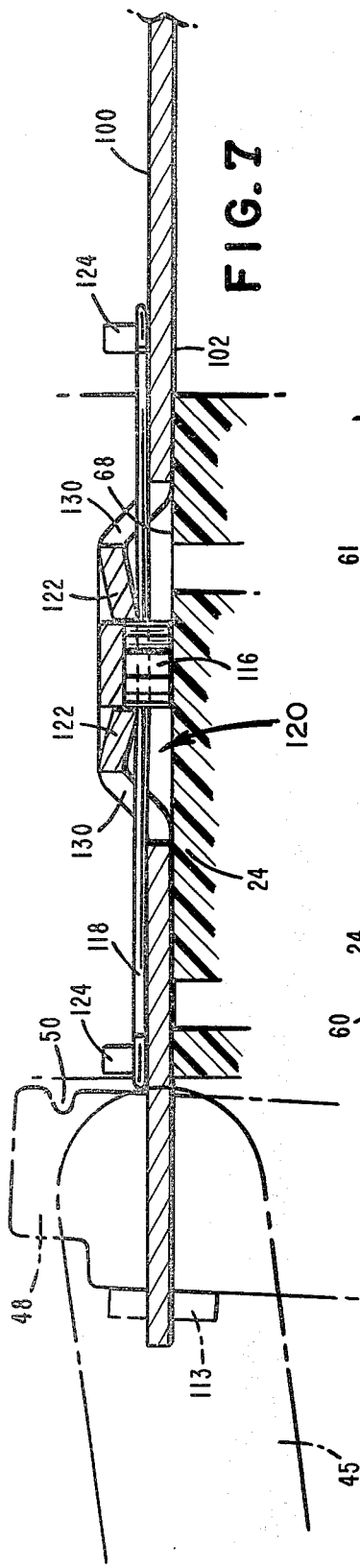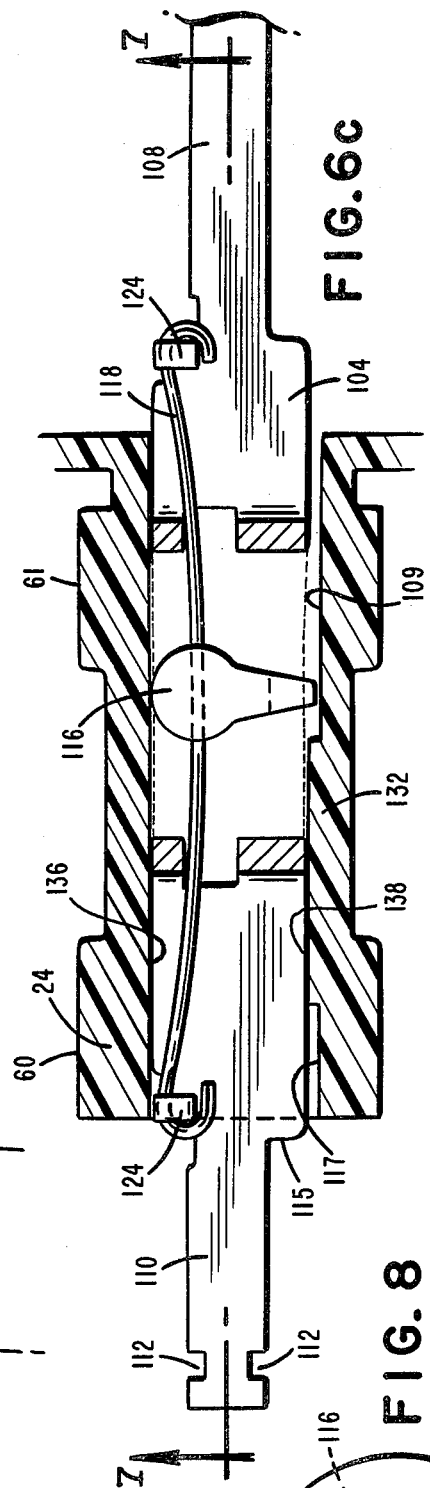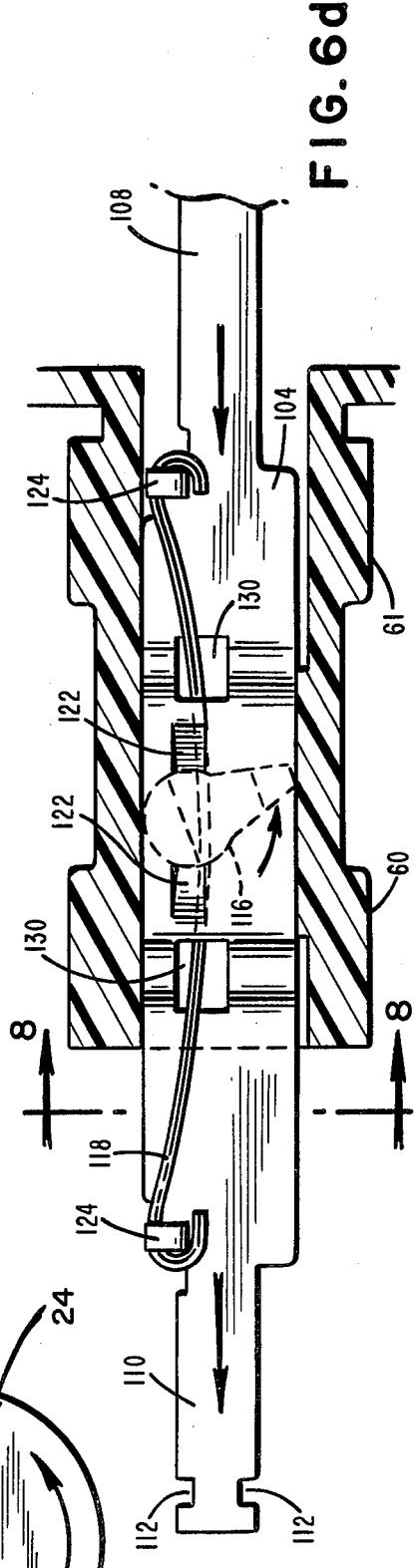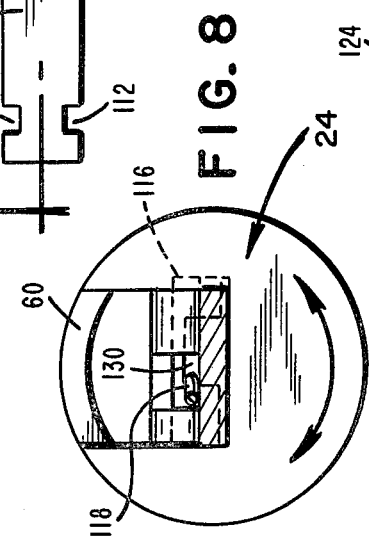

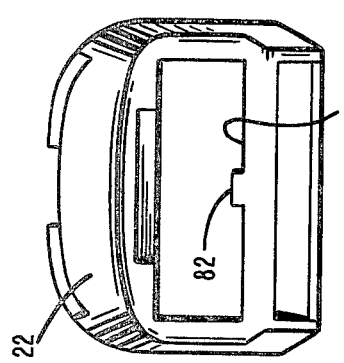
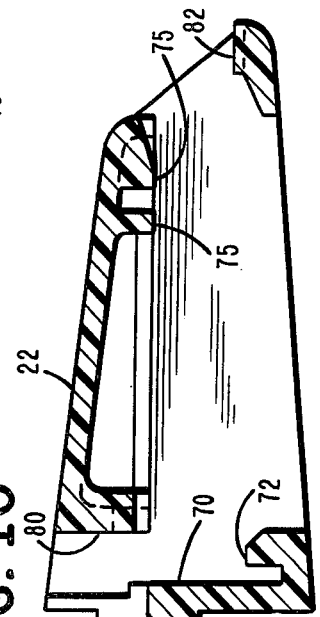
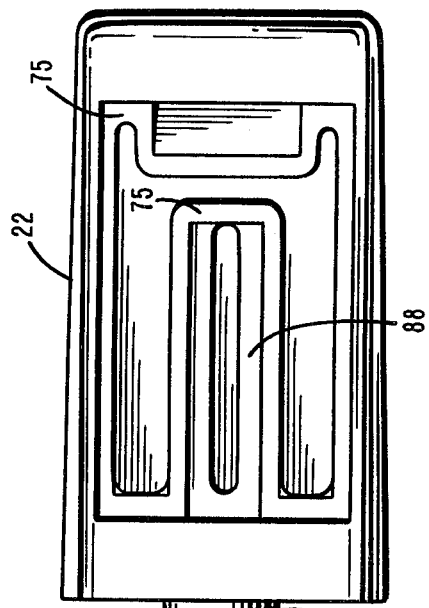
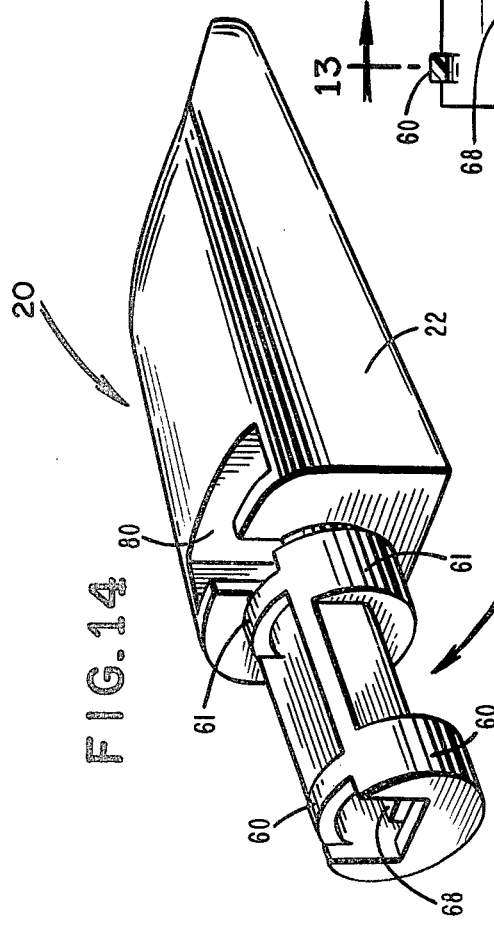
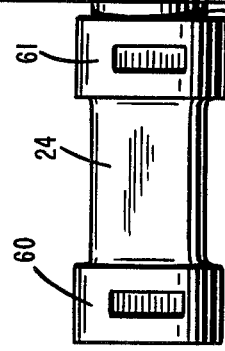
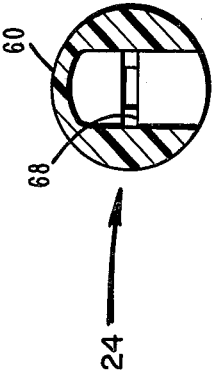

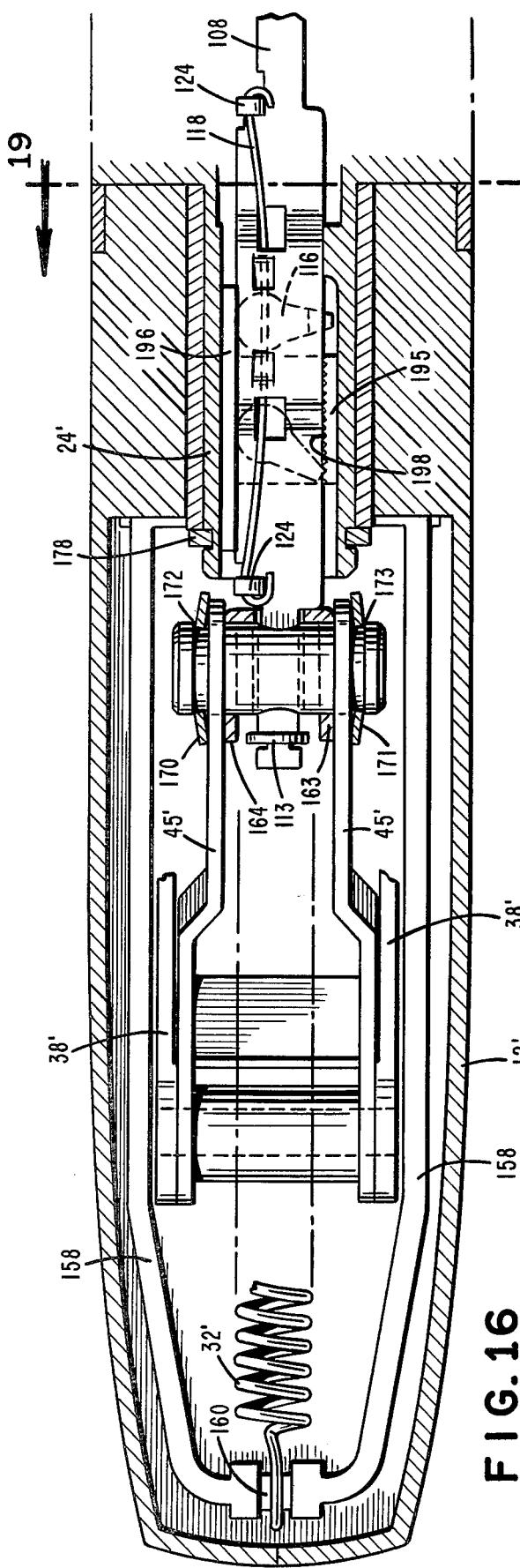
FIG. 16
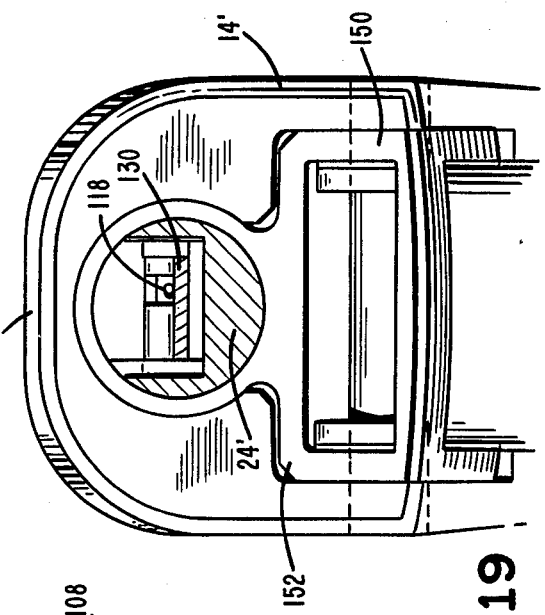
FIG. 19
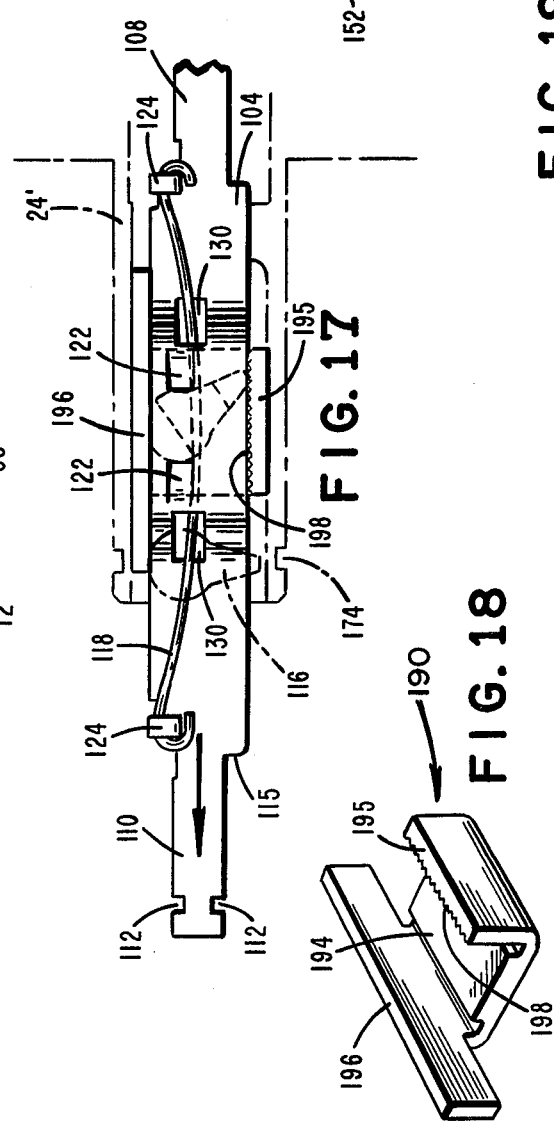
FIG. 17
FIG. 18

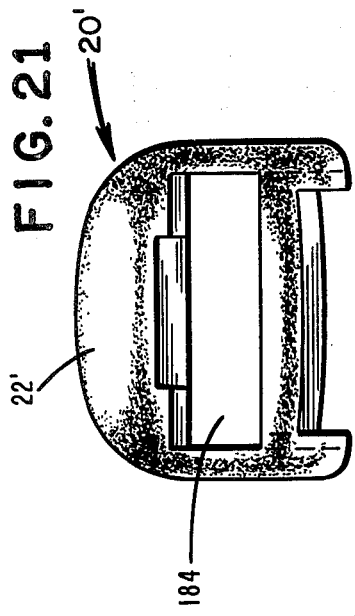
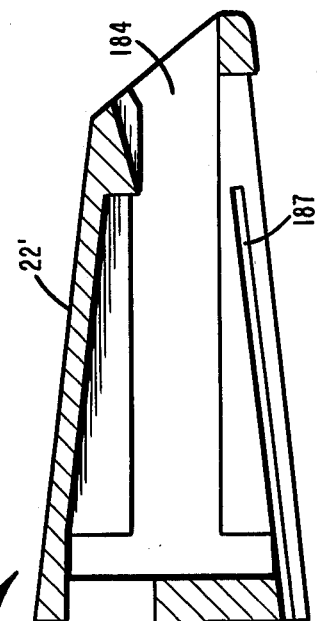
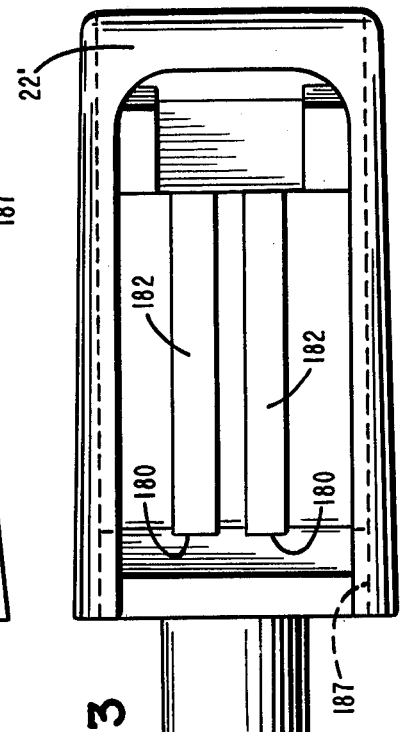
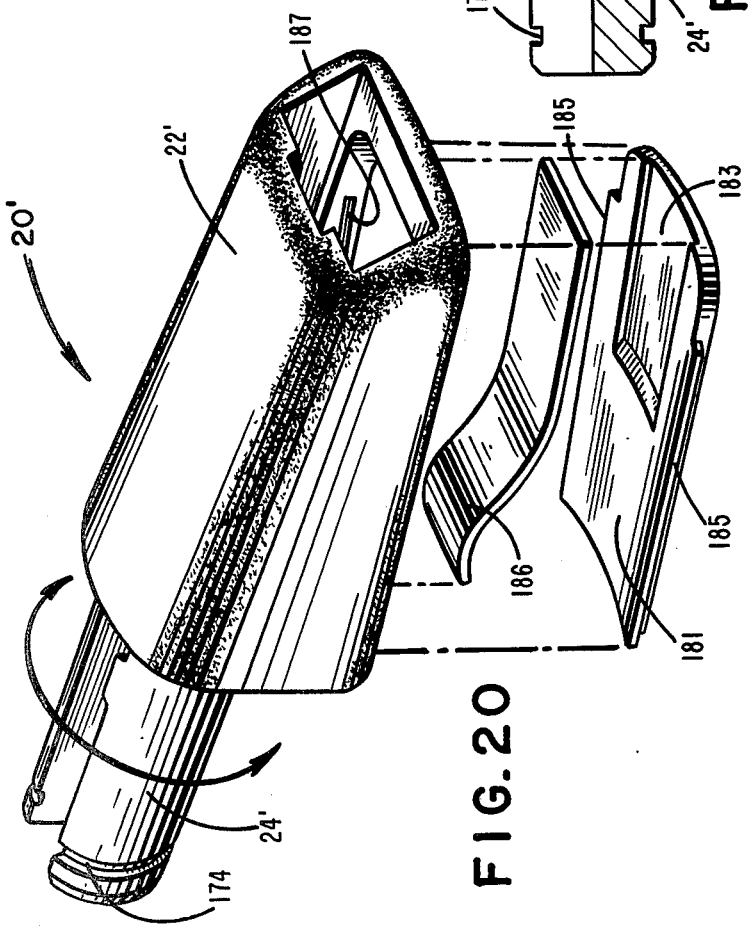
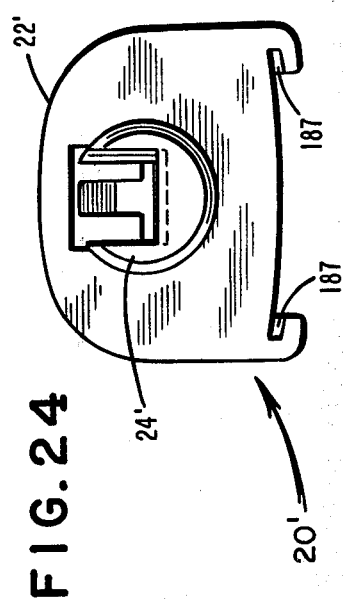

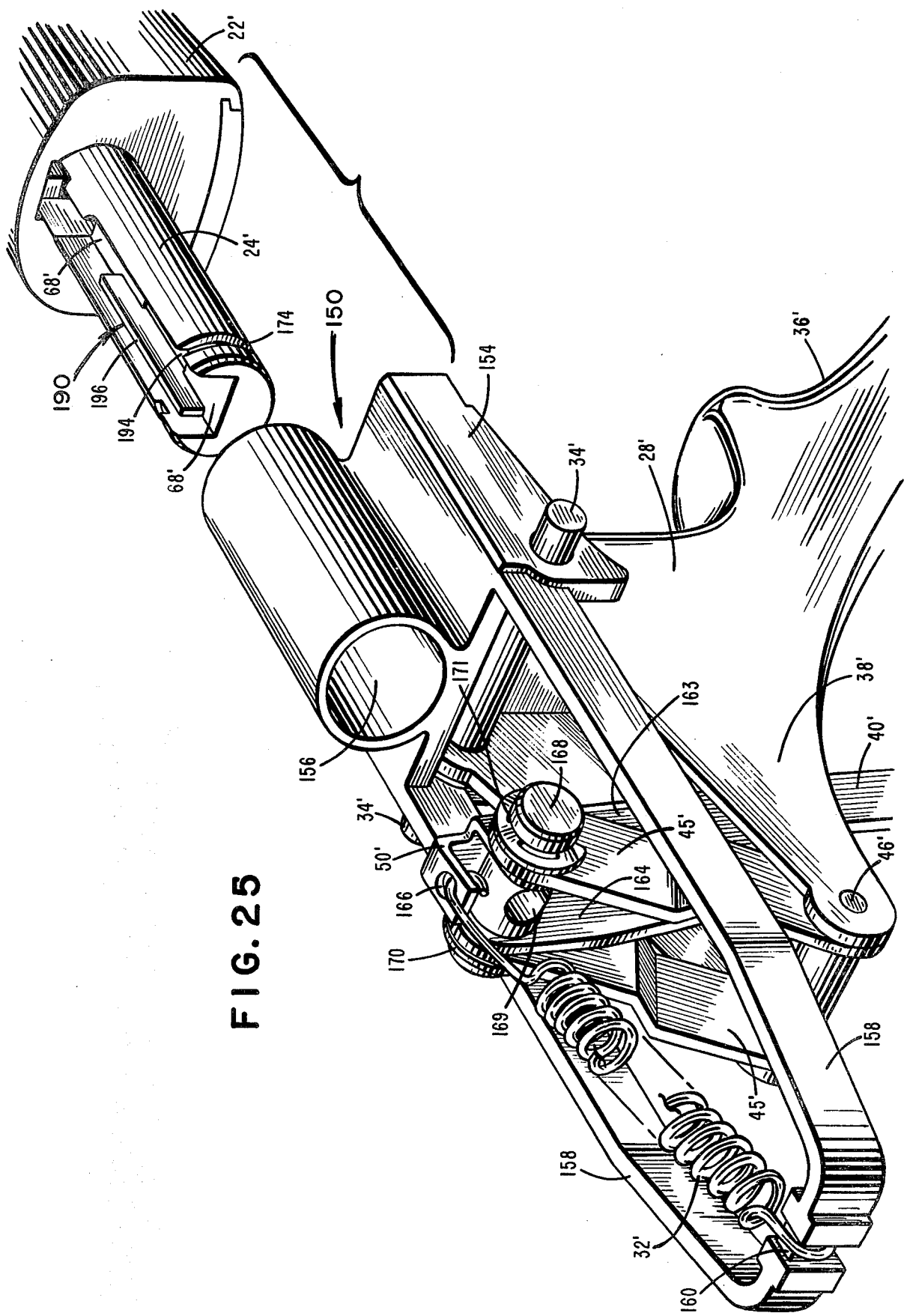

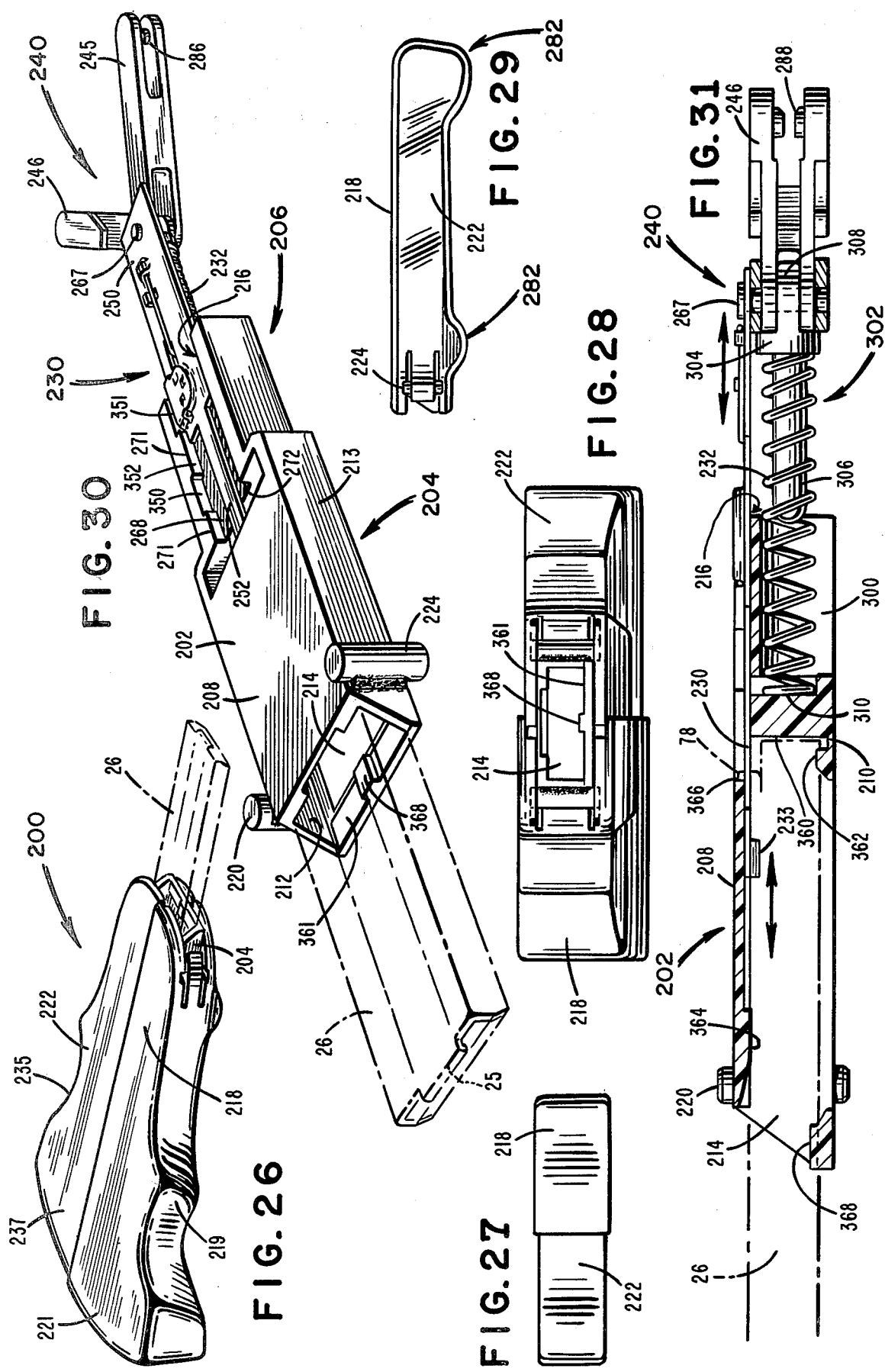

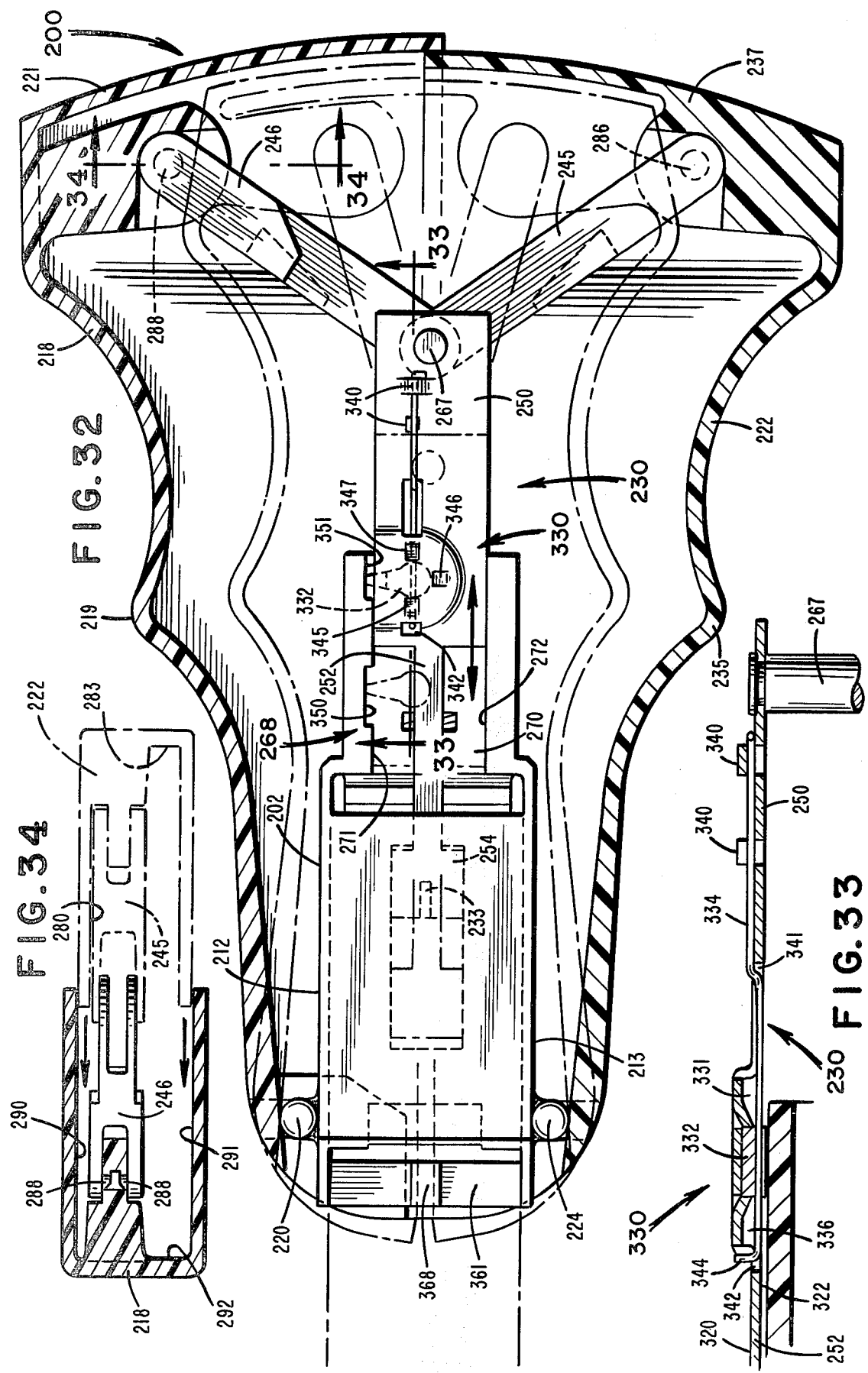

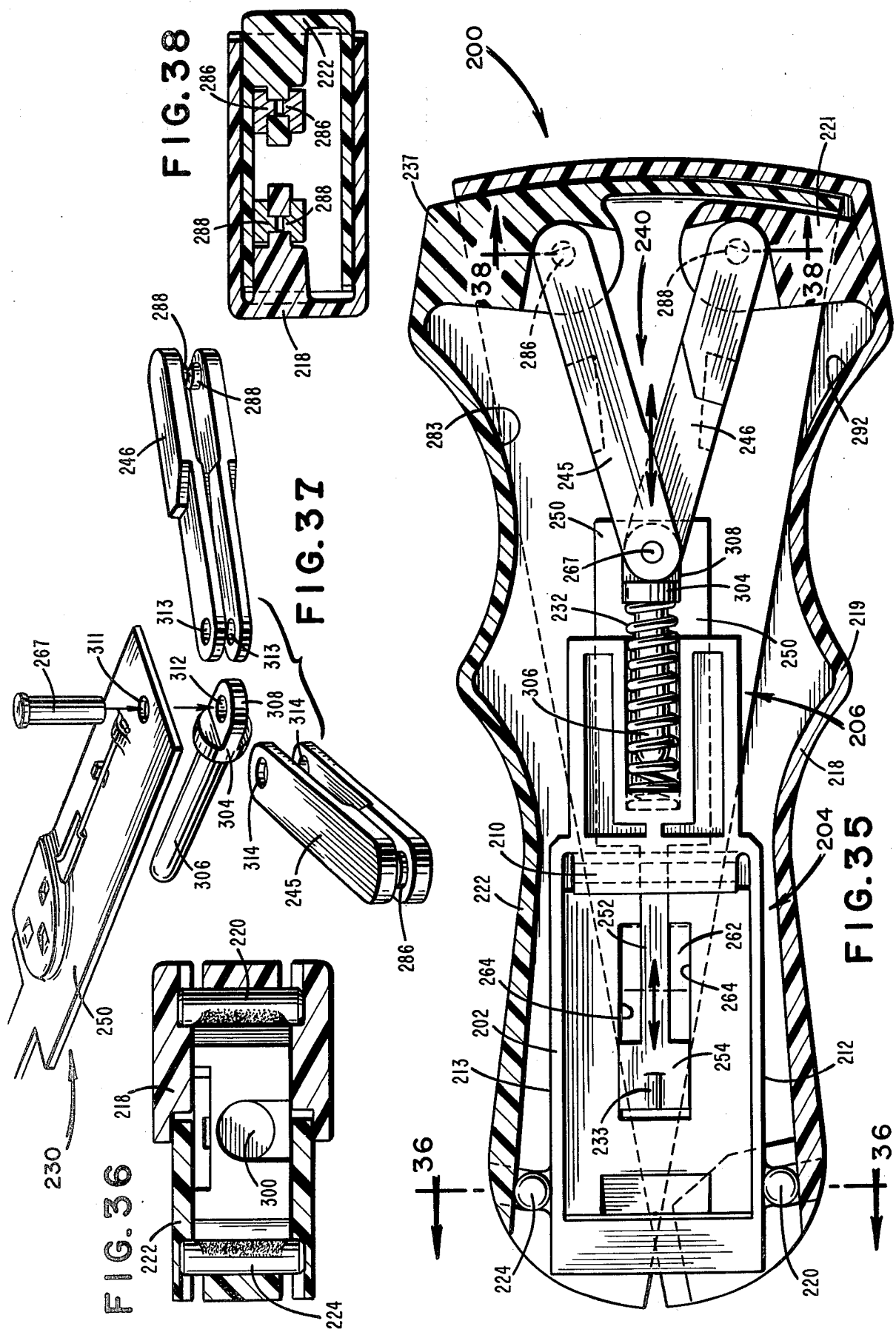

MANUALLY POWERED SURGICAL STAPLING INSTRUMENT

BACKGROUND OF THE INVENTION

1. Field of the Invention

This invention relates to a surgical instrument, in general, and to a manually-powered surgical stapling instrument for stapling together disunited segements of the external skin or internal fascia of a patient, in particular.

2. Description of the Prior Art

In U.S. Pat. No. 3,643,851, assigned to the present assignee and entitled SKIN STAPLER, there is disclosed a gas powered surgical stapler, employing a staple-carrying cartridge, for joining the disunited skin of a patient. Later developments of the gas-powered stapler and cartridges for applying surgical staples to external skin and internal fascia are disclosed in U.S. Pat. No. 3,662,939, assigned to the present assignee and entitled SURGICAL STAPLER FOR SKIN AND FASCIA.

A manually powered surgical instrument adapted to accept staple-carrying cartridges of the type disclosed in the above commonly assigned patents is disclosed in U.S. Pat. No. Re. 28,932, assigned to the present assignee and entitled SURGICAL STAPLING INSTRUMENT.

Recently, staple-carrying cartridges have been designed which eliminate the requirement for the complex gearing once needed in the powering of the surgical instrument. With these cartridges, the output shaft of the powering instrument need only have rectilinear thrust capabilities. The staples are advanced by means designed into the cartridges themselves. In commonly assigned U.S. Pat. No. 3,618,842 entitled SURGICAL STAPLING CARTRIDGE WITH CYLINDRICAL DRIVING CAMS, the advancing pusher, integral with the cartridge, rotates a pair of staple-driving screws by means of cams formed in the rear portions of the screws. In commonly assigned U.S. Pat. No. 3,638,847 entitled RACHET DRIVEN CARTRIDGE FOR SURGICAL INSTRUMENTS, the staples are driven forward by the interaction of pairs of opposing rachet teeth integral with the cartridge. In commonly assigned U.S. Pat. No. 3,650,453 entitled STAPLE CARTRIDGE WITH DRIVE BELT, the staples are driven forward by a flexible drive belt. Finally, in commonly assigned U.S. Pat. No. 3,717,294 entitled CARTRIDGE AND POWERING INSTRUMENT FOR STAPLING SKIN AND FASCIA, a flexible toothed belt is moveably housed in a main body. Staples are guided and advanced by association with spaced teeth of the flexible belt. The cartridge is equipped with an anvil integral with the main body and with a pusher which serves the functions of advancing the staples and singly ejecting and forming the same.

In U.S. Pat. No. 3,949,924, assigned to the present assignee and entitled SURGICAL STAPLING INSTRUMENT, there is disclosed a manually powered surgical instrument for stapling together disunited segments of the external skin or internal fascia of a patient.

The surgical stapling instrument of U.S. Pat. No. 3,949,924 generally comprises a main body portion having a nose portion rotatably mounted therein and adapted to receive and mount a staple-carrying cartridge. The nose portion of the stapler has the drive means for advancing and forming the staples of the cartridge mounted thereto. A pusher-activating means for driving the pusher element of the staple-carrying cartridge to advance, eject and form the staples around the anvil means of the cartridge comprises a thrust bar slidably mounted for reciprocative movement in the stapler. The thrust bar is adapted to move with a collar element slidably mounted in the stapler. A trigger means comprises a handle which is pivotally mounted on the main body portion of the stapler and has means for engaging the collar element so that the thrust bar is moved forward by squeezing the trigger to advance the staples.

An impact mechanism mounted in the stapler includes an impact spring which is loaded by squeezing the trigger and a plunger acted upon by the impact spring which is released and strikes the thrust bar when the staples are ready for ejection and forming. A return spring attached to the trigger and to the main body portion of the stapler functions to return the thrust bar to its initial position after the thrust stroke of the bar has been completed. Means are also provided for preventing more than one staple from being placed in the ready position of the staple-carrying cartridge during the stapling operation. This means comprises a clutch means which prevents the return of the thrust bar to its initial position until it has completed a full stroke, thereby ejecting a staple from the staple-carrying cartridge.

SUMMARY OF THE INVENTION

The present invention relates to a surgical instrument for stapling together disunited segements of the external skin or internal fascia of a patient.

A manually powered surgical stapling instrument is provided for applying sterilized staples to the disunited skin or fascia of a patient for affecting ajoining of the skin or fascia. The instrument is adapted to associate with a staple carrying cartridge having anvil means at one end thereof and adapted to house a plurality of staples therein. A pusher slidably mounted in the cartridge is provided for advancing the staples in the cartridge, for ejecting the staples from the cartridge and for forming the staples around the anvil. The surgical stapling instrument comprises a main body portion adapted for mounting the staple-carrying cartridge, a thrust bar mounted to reciprocate in the main body portion for driving the pusher element forward to advance, eject and form the staples, a handle arrangement for receiving a manually applied force, and a linkage arrangement for directly transmitting the manually applied force to the thrust bar to advance the thrust bar and thereby advance, eject and form the staples.

Three preferred embodiments of the subject invention are disclosed. One embodiment is for a light-weight reusable surgical stapling instrument which is highly durable. The two remaining embodiments are for light-weight single-use surgical stapling instruments which may be economically disposed or after a stapler-carrying cartridge permanently contained therein has been emptied.

In the reusable embodiment and in one disposable embodiment, there is provided a rotatably mounted nose portion. The nose portion is adapted to mount a staple-carrying cartridge so that the cartridge is rotatable therewith. In addition the nose portion is adapted to house the thrust bar so that the thrust bar is also rotatable therewith.

In each of the three embodiments, the surgical stapling instrument contains a clutch assembly which prevents the thrust bar from activating the pusher to advance, eject and form the staples more than once in each stapling operation. The clutch assembly accomplishes the above by preventing the thrust bar from returning to its initial rest position until the thrust bar has completed its forward thrust movement.

Accordingly, it is a broad object of the present invention to provide a surgical stapling instrument, which is manually powered and wholly operated by mechanical means, for stapling the disunited skin or fascia of a patient.

It is another object of the present invention to provide a light-weight surgical stapling instrument which is highly durable for continous reuse.

It is still another object of the present invention to provide a light-weight single-use surgical stapling instrument which may be economically disposed of after a staple-carrying cartridge, associated with the instrument, is empty.

It is yet another object of the present invention to provide a surgical stapling instrument which is adapted to associate with a staple-carrying cartridge requiring only rectilinear thrust capability.

It is a further object of the present invention to provide a surgical stapling instrument which is operated by a smooth and uniform manual squeezing force and which does not require an abrupt increase in squeezing force at the time of forming staples.

It is still a further object of the present invention to provide a surgical stapler in which the staple-carrying cartridge is mounted so that it is rotatable relative to the hand-held main body portion of the instrument so that the staples can be applied at any angle without the necessity for rotating the hand-held portion of the instrument.

Another object of the present invention is to provide a surgical stapler with means for ensuring that the staple-advancing drive means of the instrument is activated only once in each stapling operation.

These and other objects of the invention, as well as many of the attendant advantages thereof, will become more readily apparent when reference is made to the following description taken in conjunction with the accompanying drawings.

BRIEF DESCRIPTION OF THE DRAWINGS

FIG. 1 is a side elevation of a first embodiment of the subject invention.

FIG. 1a is a pictorial representation in phantom line of the rear end of a staple-carrying cartridge.

FIG. 2 is a longitudinal section of the embodiment illustrated in FIG. 1.

FIG. 2a is a front elevation of the main body portion, showing the rear portion of the nose in section, as viewed along line 2a—2a of FIG. 2.

FIG. 3 is a top plan of the first embodiment with the cover removed.

FIG. 4 is an exploded perspective showing the relationship between the link, the rocker arm, the trigger, the thrust bar, and the clutch assembly.

FIG. 5 is a detailed perspective of the bias spring and pawl of the FIG. 4 clutch assembly.

FIGS. 6a through 6d illustrate in enlarged top plan the operation of the thrust bar and clutch assembly; FIG. 6a shows the thrust bar in its initial position, FIG. 6b shows the thrust bar in its mid-forward position,
FIG. 6c shows the thrust bar in its position at the completion of a staple-forming operation, and FIG. 6d shows the thrust bar in its mid-return position.

FIG. 7 is a longitudinal section of the thrust bar and clutch assembly taken along line 7—7 of FIG. 6c.

FIG. 8 is a cross section taken along line 8—8 of FIG. 6d.

FIGS. 9–14 illustrate the nose portion of the first embodiment; FIG. 9 is a front elevation, FIG. 10 is a longitudinal section, FIG. 11 is a bottom plan, FIG. 12 is a cross section taken along line 12—12 of FIG. 10, FIG. 13 is a cross section taken along line 13—13 of FIG. 10, and FIG. 14 is a perspective view.

FIG. 16 is a longitudinal section through the main body portion of the embodiment illustrated in FIG. 15, with the drive mechanism shown in top plan.

FIG. 17 is a top plan of the thrust bar of FIG. 16.

FIG. 18 is a perspective of the thrust plate of FIG. 16.

FIG. 19 is a front elevation of the main body portion viewed along line 19—19 of FIG. 16.

FIGS. 20–24 illustrate the nose portion of the second embodiment; FIG. 20 is an exploded perspective of the nose, leaf spring, and bottom cover plate, FIG. 21 is a front plan, FIG. 22 is a longitudinal section, FIG. 23 is a bottom plan, and FIG. 24 is a rear elevation.

FIG. 25 is a pictorial perspective of the second embodiment with the housing and the thrust bar removed, and the nose portion advanced out of the cradel.

FIG. 26 is a pictorial perspective of a third embodiment of the subject invention.

FIG. 27 is a rear elevation of the embodiment shown in FIG. 26.

FIG. 28 is a front elevation of the third embodiment.

FIG. 29 is a side elevation of the third embodiment.

FIG. 30 is a perspective of the third embodiment with the handle removed.

FIG. 31 is a longitudinal section of the embodiment shown in FIG. 30.

FIG. 32 is a top plan of the thrust bar shown in FIG. 30 in association with the handles.

FIG. 33 is a longitudinal section of the thrust bar shown taken along line 33—33 of FIG. 32.

FIG. 34 is a cross section of the handles and links of the third embodiment taken along line 34-34 of FIG. 32.

FIG. 35 is a bottom plan of the third embodiment with the thrust bar fully advanced and with the handles shown in section.

FIG. 36 is a cross section through the hinges for the handles as view along line 36—36 of FIG. 35.

FIG. 37 is an exploded perspective of the links, the thrust bar, the connecting pin, and the hinge pin.

FIG. 38 is a section through the handles and link taken along line 38—38 of FIG. 35.

DESCRIPTION OF THE PREFERRED EMBODIMENTS

Figure 15:
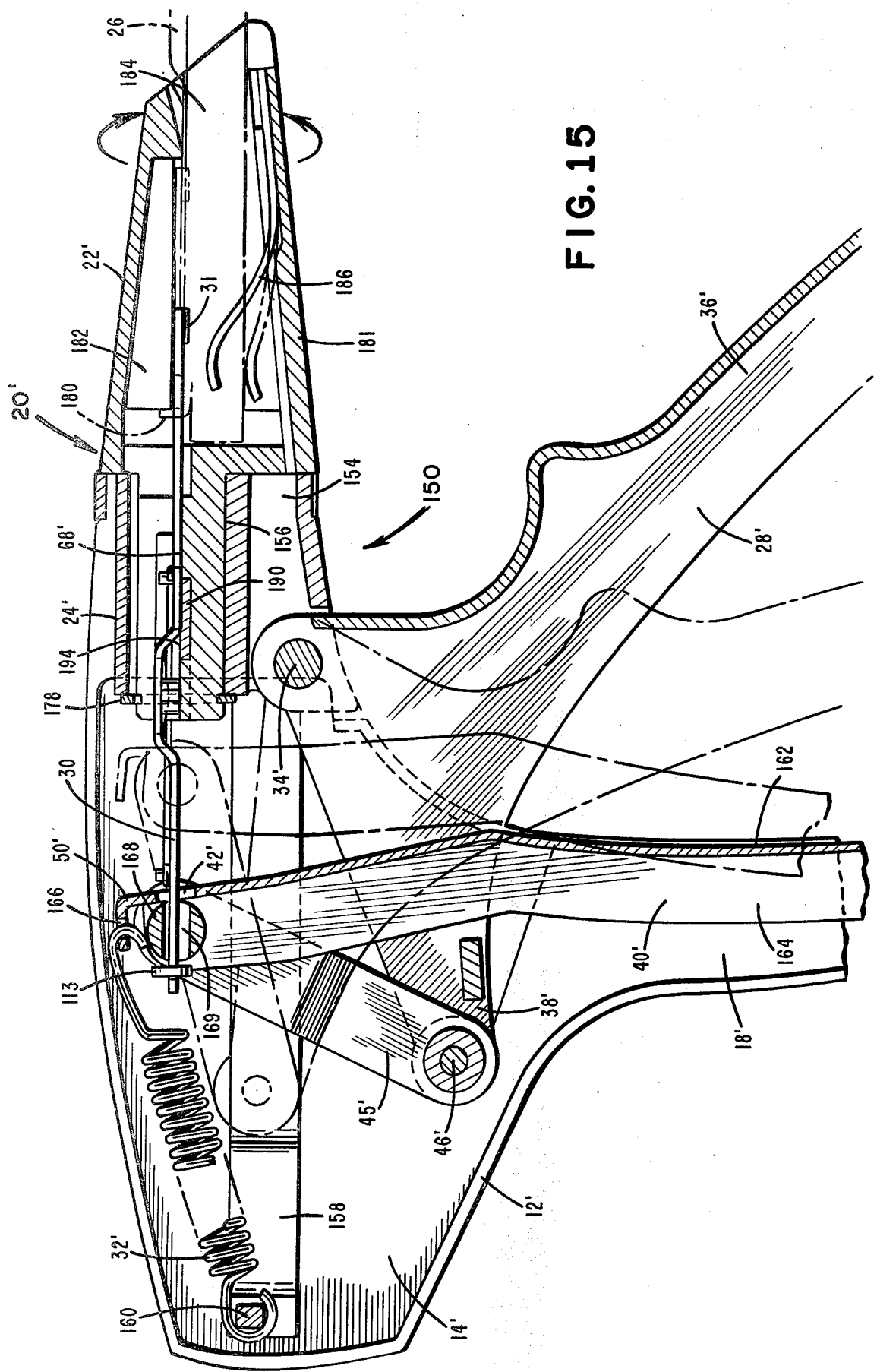
FIG. 15 is a longitudinal section of a second embodiment of the subject invention.

In describing the preferred embodiment of the invention illustrated in the drawings, specific terminology will be resorted to for the sake of clarity. However, it should be understood that the invention is not to be limited to the specific terms so selected, and it is to be understood that each specific term includes all technical equivalents which operate in a similar manner to accomplish a similar purpose.

A first embodiment of the surgical stapler of the present invention will be described in general with reference to FIGS. 1 and 2. This embodiment provides the surgeon with a compact, disposable unit made up of a surgical stapler with a staple-carrying cartridge already mounted therein. Unless specified otherwise, the components constituting the surgical stapler are made from a suitable plastic, such as ABS resin. The surgical stapler, shown generally at 10, comprises housing 12 having main body portion 14, cover portion 16 and handle portion 18. Nose portion 20 includes a front section 22 extending out of housing 12 and adapted to mount staple-carrying cartridge 26. Nose portion 20 further includes a rear section 24, located inside housing 12 and acting to mount a stainless steel thrust bar 30 for advancing, ejecting and forming staples from the staple-carrying cartridge. The staples are formed about an anvil 25, which is an integral part of the staple-carrying cartridge 26.

The staples in staple-carrying cartridge 26 are advanced, ejected and formed by mechanical means only. Accordingly, the power for advancing, ejecting and forming the staples in cartridge 26 comes from the manipulative force supplied to stapler 10 by the surgeon. This force is transmitted to the drive means of stapler 10 by means of a trigger 28 which generally comprises a handle pivotably attached to housing 12. Pivoting of trigger 28 causes the thrust bar 30 to drive the pusher element 27 of stapler-carrying cartridge 26 forward to carry out a staple forming operation which comprises advancing, ejecting and forming the staples. At the conclusion of a staple forming operation, a stainless steel return spring 32, cooperating with the thrust bar 30 and attached to the housing 12, returns the thrust bar and the trigger to their initial positions for the next stapling cycle.

With reference now to FIGS. 1, 2 and 4, trigger 28 will be described. Trigger 28 is pivotally mounted to housing 12 by means of pivot pin 34. Trigger 28 is of appropriate size and shape to be conveniently gripped by the operating hand of the surgeon. Trigger 28 is of L-shape and includes a lower hand-engaging portion 36 and an upper force-transmitting portion 38.

A rocker arm 40 is pivotally mounted within the housing 12 by a pivot pin 41. As best shown in FIGS. 2, 3 and 4, the rocker arm contains a bore 42 for receiving the rear end 110 of the thrust bar 30. An H-frame link 45 is provided for transmitting to the thrust bar 30, via the rocker arm 40, the manual force applied to the trigger 28. One end of link 45 is pivotally mounted to the free end of the force-transmitting portion 38 by a pair of projections 46. The other end of link 45 is pivotally mounted to the rocker arm 40 by a pair of projections 47, which are best shown in FIGS. 3 and 6a through 6d. Extending from the upper end of rocker arm 40 is a spring retaining member 48, having a lip 50 for facilitating attachment of one end of return spring 32. The other end of return spring 32 is received in a recess 52 in the housing 12. The cover 16, when secured to the lower portion of the housing ensures the permanent attachment of the return spring 32 to the housing 12. The cover 16 is attached to the lower portion of the housing by suitable fasteners, such as the three screws 5–7.

The rotatably mounted nose 20 will now be described with reference to FIGS. 2, 3 and 9–14. The nose 20 comprises a front section 22 and a rear section 24. The top rear portion of the front section 22 contains a cutout 35 which receives a cover member 33. The cutout 35 and the cover member 33 act to facilitate assembly of the nose 20 during manufacture. The forwardmost end of housing 12 is defined by a wall 54, which has a cylindrical inner ring 82. The rear portion 24 of the nose 20 is generally of cylindrical shape and contains an annular groove 84. The wall 54 and inner ring 82 constitute a rotation guide member. When the nose 20 is mounted within the housing 12, the rotation guide member cooperates with the annular groove 84 to permit axial rotation of the nose, while at the same time preventing axial translation of the nose within the housing 12.

With the cover 16 in place, the housing 12 contains cylindrical inner surfaces 56, 57 and 58, which are adapted to mate in a bearing relationship with cylindrical outer surfaces 60–61 formed on the rearward portion 24 of the nose 20. These bearing surfaces provide the means for mounting the nose 20 within the housing 12, and the means for permitting the axial rotation of the nose with respect to the housing 12. The rearward portion 24 is generally hollow and contains a longitudinally extending slot 68 for receiving the thrust bar 30.

As best seen in FIGS. 2 and 9 through 11, the front portion 22 of the nose is adapted to permanently hold the staple-carrying cartridge 26. A stop provided by wall 70 limits the extent to which the cartridge may be inserted into the nose 20. The staple-carrying cartridge 26 is held in place within the nose 20 by upwardly extending ledges, 72 and 73, and a downwardly extending rib structure 75, containing a number of longitudinal and transverse sections. The staple-carrying cartridge 26 (see FIG. 1a) has a pair of upwardly extending, spaced tabs 78 at its rear end. The spacing between tabs 78 is sufficient to allow the narrow portion 31 of the thrust bar 30 to freely slide therebetween, and tabs 78 are dimensioned so as to fit up against the wall 80 near the rearwardmost end of the rib structure 75. An upwardly projecting key 82, contained on ledge 73, is received in a mating recess in the staple-carrying cartridge 26. When tabs 78 are properly positioned and key 82 is mated with recess, the staple-carrying cartridge 26 cannot be inadvertently pulled out of nose portion 20 of stapler 10, and cartridge 26 is fixed against forward movement during the stapling operation. A recess or guideway 88 is provided to slidably receive a portion of the thrust bar 30. This guideway maintains the thrust bar 30 in intimate contact with the top surface of the staple-carrying cartridge 26.

The thrust bar assembly will now be described with reference to FIGS. 4, 5 and 6a through 6d. The thrust bar 30 is an elongated substantially planar member comprising an upper surface 100 and a lower surface 102. In addition, the thrust bar contains a body 104, a head 106 coupled to the body by a narrow midsection 108, and a narrow end 110, extending from the rear end of the body. The width of the head 106 is chosen to allow free movement within the guideway 88 provided in the nose portion 20. The width of the narrow midsection 108 is chosen to allow free movement between the cartridge tabs 78. The width of the body 104 is chosen to allow free movement within the slot 68 provided in the rear portion 24 of nose 20. The width of the leg 110 is chosen to allow that section to be rotatably mounted within the bore 42 of the rocker arm 40. The end 110 defines a pair of notches 112 for receiving a fastener 113 to prevent the rocker arm 40 from drawing away from the thrust bar 30 under the influence of return spring 32.

Mounted on the body 104 of the thrust bar 30 is a clutch assembly noted generally as 114 in FIG. 5. Clutch assembly 114 consists of a stainless steel pawl 116 and a stainless steel bias spring 118. Returning now to FIGS. 4 and 7, the thrust bar 30 contains four bends to create, below the bottom surface 102 of the thrust bar, an open area 120 for receiving the pawl 116. A pair of downwardly projecting fingers 122 are provided to confine the pawl 116. A pair of upwardly projecting fingers 124 are provided as a means for mounting the ends of the bias spring 118. The pawl is inserted between the downwardly projecting fingers so that the flat portion of the pawl is against the lower surface 102 of the thrust bar 30, as illustrated in FIGS. 7 and 6c.

Each free end of the bias spring 118 is fixedly attached to one of the projections 124. The length of the spring 118 passes through a pair of thrust bar apertures 130, thus engaging the pawl 116 between the spring 118 and the bottom surface in the open area 120. The bias spring 118 is used to maintain the pawl in a generally transverse position with respect to the axis of the thrust bar 30 as shown in FIG. 6c. As can be seen, the longitudinal dimension of the pawl is slightly larger than the transverse dimension of the thrust bar.

The operation of the clutch assembly will now be described with reference to FIGS. 6a through 6d, and 7. Contained within the rear portion 24 of the nose 20 is a outwardly extending longitudinal projection 132 which is defined by cut-out portions 117 and 119, and which is in the same plane as the pawl 116, when the thrust bar is slidably mounted in the slot 68 (FIGS. 6a-6d). The length of the projection 132, defined between the cut-outs 117 and 119, is slighly shorter than the distance travelled by the thrust bar 30, during a staple forming operation. When the thrust bar 30 is in its ready position (FIG. 6a), the pawl 116 is located to the left of the projection 132. When a stapling operation begins (FIG. 6b), the thrust bar is moved to the right. When the pawl encounters the projection, the tip of the pawl is caused to move in a direction opposite to that traveled by the thrust bar. If movement of the thrust bar is interrupted before the completion of the stapling operation, the pawl will be located between the wall 136 of the slot 68 and the surface 138 provided by the projection. Return spring 32 provides tension to try and return the thrust bar to its ready position. The tip and rounded portion of the pawl 122 are wedged between the wall 136 and the projection surface 138 to prevent this action from taking place. Thus, a complete stapling cycle must be completed before the thrust bar 30 can be returned to its ready position.

Once a staple-forming operation has been completed (FIG. 6c), the pawl 116 is located in an area to the right of the projection 132. At the completion of the staple-forming operation, the pawl, under the urging of the bias spring 118, is in a generally transverse position with respect to the longitudinal axis of the thrust bar 30. The thrust bar is then free to return to its ready position in response to the force exerted by return spring 32. While this takes place (FIG. 6d), the tip of the pawl 116 is deflected by the projection 132 in a direction opposite to that traveled by the thrust bar. If a surgeon attempts to initiate a stapling operating during the return trip of the thrust bar, the pawl restricts the movement of the thrust bar. When tension on the trigger 28 is removed, the thrust bar 30 continues its return trip to the ready position. Thus the clutch assembly acts to prevent the occurrence of staple jams in the staple cartridge.

The operation of the stapling instrument 10 will now be described with reference to FIGS. 1, 2 and 3. For use, the disposable plastic stapling instrument 10 comes with a staple-carrying cartridge 26 already in place. The instrument is actuated by squeezing the trigger 28 toward the handle 18. Upon initial actuation of the trigger 16, the upper force-transmitting portion 38 rotates in a clockwise direction about pivot pin 34. The arcuate movement of the force-transmitting portion 38 is transferred to the rocker arm 40 via the link 45. In response thereto, the rocker arm 40 rotates in a clockwise direction about the pivot pin 41. As the rocker arm 40 pivots, it presses up against the thrust bar along shoulder 115 of the body 104. The thrust bar 30 responds by moving in a forward direction within the slot 68, provided in the rear-portion 24 of the nose 20. At the same time, the return spring 32 is caused to extend from its relaxed position by the movement of rocker arm 40; thus providing a return tension on the rocker arm. The tab 31 of the thrust bar 30 causes the pusher 27 of the staple-carrying cartridge 26 to initiate the stapling cycle. The mechanism within the staple-carrying cartridge 26 responds to the rectilinear thrust capabilities of the subject invention by advancing, ejecting and forming the surgical staples stored in the cartridge. During the staple forming operation, the clutch assembly operates as described hereinbefore.

At the conclusion of the staple forming operation, the tension provided by the return spring 32 causes the rocker arm 40 to pivot in a counter-clockwise direction about pivot pin 41 and thereby draw the thrust bar 30 to its ready position. The movement of the rocker arm, also, causes the trigger 28 to return to its ready position via the movement of the link 45.

With reference to FIG. 1, the increasing mechanical advantage as the forward stroke progresses can be understood. This increase in mechanical advantage is desired because the greatest amount of work, that of forming the staple, occurs during the last fraction of stroke of the thrust bar 30. As the trigger 28 rotates clockwise about center 34, the positional relationship between the trigger, link 45 and the thrust bar 30 change so that center 47 approaches the line connecting centers 34 and 46. This change in relationship follows the well-known principle of the toggle mechanism. If the displacement is carried out so that center 47 comes very close to the line between centers 34 and 46, the mechanical advantage of the toggle theoretically approaches infinity.

With reference to FIGS. 1, 2 and 8, the nose portion 20 is fully rotatable within the housing 12. A rotation of the nose portion also rotates the thrust bar 30 and the staple-carrying cartridge 26. The thrust bar 30 is permitted to rotate because of the bore 42 within the rocker arm. Thus, the staple cartridge may be rotated into any position, as determined by the surgeon, during the use of the stapling instrument.

A second embodiment of the subject invention will now be described with reference to FIGS. 15 through 25. This embodiment operates in a matter similar to that of the first embodiment; the major difference being structural. Since this embodiment is for a permanent rather than a disposal stapling instrument, all of the instrument's components, unless specified otherwise, are made of stainless steel.

The stapler shown generally at 10' in FIG. 15 comprises housing 12' having a main body portion 14' and handle portion 18'. Nose portion 20' includes a front section 22' extending out of housing 12' and adapted to mount staple-carrying cartridge 26. Nose portion 20' further includes a rear section 24' located inside housing 12' and acting to mount the thrust bar 30 for advancing, ejecting and forming staples from the staple-carrying cartridge 26.

The staples in the staple-carrying cartridge 26 are advanced, ejected and formed by mechanical means in a manner similar to that previously described concerning the first embodiment. Thus, the power to carry out a staple-forming operation comes from the manipulative force supplied to the stapler 10' by the surgeon. This force is transmitted to the drive means of stapler 10' by means of a trigger 28' which generally comprises a handle pivotably attached to a cradle structure 150, forming part of the housing 12'. Pivoting the trigger 28' causes the thrust bar 30 to drive the pusher 27 (see FIG. 1a) of the staple-carrying cartridge 26 forward to carry out a staple-forming operation. At the conclusion of a staple-forming operation, a return spring 32', cooperating with the thrust bar 30 and attached to the cradle 150, returns the thrust bar to its ready position for the next stapling cycle.

To keep the overall weight of the stapler 10' to a minimum, the housing 12' takes the form of a thin stainless steel shell. As shown in FIG. 19, at the front portion of the main body 14' there is a longitudinally extending cavity 152 defined within the housing 12'. Fixedly mounted within the cavity is the cradle structure, generally designated as 150. As best seen in FIGS. 15, 19 and 25, the cradle structure 150 comprises a body portion 154 configured to be fixedly mounted within the cavity 152. A longitudinally extending bore 156 in the cradle is provided to receive the rear portion 24' of the nose. Extending from the rear portion of the cradle body are a pair of elongated longitudinally extending arms 158. The free ends of the arms 158 are joined together by a pin 160.

With reference now to FIGS. 15 and 25, trigger 28' will be described. Trigger 28' is pivotally mounted to the cradle body 150, which forms part of the housing 12', by means of a pivot pin 34'. Trigger 28' is of appropriate size and shape to be conveniently gripped by the operating hand of the surgeon. Trigger 28' is of L-shape and includes a lower hand-engaging portion 36' and an upper force-transmitting portion 38'.

A rocker arm 40' is pivotally mounted within the housing 12' by a pivot pin 41'. It is to be understood that the bottom part of rocker arm 40' and the pivot pin 41' are similar to the bottom part of rocker arm 40 and the pivot pin 41 as shown in FIG. 1. The rocker arm is formed by a foundation wall 162 and a pair of side walls 164. Extending from the upper end of the rocker arm 40' is a spring retaining member 50', having a aperture 166 for facilitating attachment of a free end of the return spring 32' to the member 50'. The other end of return spring 32' is attached to the cradlearm pin 160.

A pair of links or couplers 45' is provided for transmitting to the thrust bar 30 the manual force applied to the trigger 28'. One end of the link pair 45' is pivotally mounted to the free end of the force-transmitting portion 38' by a pivot pin 46'. The other end of the link pair is pivotally mounted to the rocker arm 40' by a pivot pin 168. The pivot pin 168 contains a transversely extending bore 169, which is brought into registry with a foundation wall aperture 42' to provide an opening for receiving the rear end 110 of the thrust bar 30. The pivot pin 168 is held in place by a pair of fasteners, 170 and 171, which are received in pivot-pin grooves 172 and 173, respectively.

The rotatably mounted nose 20' will now be described with reference to FIGS. 15 and 20 through 25.

The nose 20' comprises a front section 22' and a rear section 24'. A longitudinally extending slot 68' through the front and rear portions of the nose provides a guide way for the thrust bar 30. The rear portion 24' is generally of cylindrical shape; the outer diameter of the rear portion being chosen to be slidably and rotatably mounted in the cradle bore 156. At the end of the rear portion is an annular groove 174, which receives a ring 178 for holding the nose within the cradle bore.

With reference now to FIGS. 15 and 20 through 24, the association of the staple-carrying cartridge 26 and the rotatable nose 20' will now be described. The staple-carrying cartridge 26 is detachably mounted on nose portion 20'. Staple-carrying cartridge 26 (see FIG. 1a) is elongated and has a pair of upwardly extending spaced tabs 78 at its rear end. The spacing between tabs 78 is sufficient to allow the narrow portion 31 of the thrust bar 30 to freely slide therebetween, and tabs 78 are dimensioned so as to fit into slots 180 near the rearwardmost end of locater plate 182. Therefore, when tabs 78 are properly positioned, staple-carrying cartridge 26 cannot be inadvertently pulled out of nose portion 20' of stapler 10', and cartridge 26 is fixed against forward movement during the stapling operation.

Staple-carrying cartridge 26 is mounted in stapler 10' by inserting the end of cartridge 26 into opening 184 in nose portion 20'. The rearward end of staple-carrying cartridge 26 engages a leaf spring 186 which urges the cartridge 26 upwardly until tabs 78 are positively locked into their associated openings 180 in locator plate 182. With cartridge 26 in this position, pusher-engaging tab 31 is engaged with the staple pusher 27 of cartridge 26. The locator plate 182 maintains the thrust bar 30 in intimate contact with the top surface of the staple-carry cartride 26. The cartridge 26 is removed from the stapler 10, when exhausted of staples, by reversing the insertion steps.

As shown in FIG. 20, a cover 181, contains a recess 183 in which the leaf spring 186 is fixedly mounted. A pair of slide members 185, extending from the cover 181, are received in a pair of mating slots 187 (see FIG. 24) to facilitate mounting the cover to the bottom of the front portion 22' of the nose 20'. It is to be understood that the front portion 22' may be one piece thereby eliminating the need for the cover 181.

The thrust bar 30 and the clutch assembly 114 of stapler 10' are of the same configuration and structure as the thrust bar and the clutch assembly previously described with reference to surgical stapler 10. Thus, like elements are denoted by like reference numerals.

The operation of the clutch assembly 114 will now be described with reference to FIGS. 16 and 17. It should be noted, at this point, that the operation of the thrust bar and the clutch assembly of stapler 10' is, except as noted below, the same as the operation of the thrust bar and the clutch assembly previously described with reference to surgical stapler 10 and FIGS. 6a through 6d. A thrust plate 190 is adapted to be fixedly positioned in slot 68', provided in the rear portion 24' of the nose 20'. The thrust plate comprises a base 194 and two side walls, 195 and 196. Side wall 195 contains a serrated surface 198. The thrust plate 190 is mounted within the slot 68' so that the thrust plate base 194 forms a continuation of the thrust bar slot 68'. The length of side wall 195 is slightly shorter than the distance travelled by the thrust bar 30 during a staple forming operation. When the thrust bar 30 is in its ready position, the pawl 116 is located to the left of side wall 195. When a stapling operation begins, the thrust bar is moved to the right. When the pawl 116 encounters the side wall 195, the tip of the pawl is caused to move in a direction opposite to that travelled by the thrust bar. If movement of the thrust bar 30 is interrupted before the completion of the stapling operation, the pawl 116 will be located between the wall 196 of the thrust plate 190 and the serrated surface 198 provided by the sidewall 195. Return spring 32' provides tension to try and return the thrust bar to its ready position. The tip and rounded portion of the pawl 116 are wedged between the wall 196 and the serrated surface 198 to prevent this action from taking place. Thus, a complete stapling cycle must be completed before the thrust bar 30 can be returned to its ready position.

Once a staple forming operation has been completed, the pawl 116 is located in an area to the right of the side wall 195. At the completion of the staple forming operating, the pawl, under the urging of the bias spring 118, is in a generally tranverse position with respect to the longitudinal axis of the thrust bar 30. The thrust bar is then free to return to its ready position in response to the force exerted by return spring 32'. While this takes place, the tip of the pawl 116 is deflected by the wall 195 in a direction opposite to that travelled by the thrust bar. If a surgeon attempts to initiate a stapling operation during the return trip of the thrust bar, the pawl 116 restricts the movement of the thrust bar. When tension on the trigger 28' is removed, the thrust bar 30 continues its return trip to the ready position. Thus, the clutch assembly acts to prevent the occurrence of staple jams in the staple cartridge.

The operation of the stapling instrument 10' can best be seen with reference to FIGS. 15 and 16. A staple-carrying cartridge 26 is mounted on nose portion 20' in the manner as described hereinbefore. The reusable stainless steel stapling instrument 10' is actuated by squeezing the trigger 28' toward the handle 18'. Upon initial actuaton of the trigger 28', the upper force-transmitting portion 38' rotates in a clockwise direction about pivot pin 34'. The arcuate movement of the force-transmitting portion 38' is transferred to the rocker arm 40' via link pair 45'. In response thereto, the rocker arm 40' rotates in a clockwise direction about the pivot pin 41'. As the rocker arm 40' pivots, it presses up against the thrust bar at shoulder 115 of the body 104. The thrust bar 30 responds by moving in a forward direction within the guideway 68', provided in the rear-portion 24' of the nose 20'. At the same time the return spring 32' is caused to extend from its relaxed position by the movement of rocker arm 40'; thus providing a return tension on the rocker arm. The tab 31 of the thrust bar 30 causes the pusher 27 of the staple-carrying cartridge 26 to initiate the stapling cycle. The mechanism within the staple-carrying cartridge 26 responds to the rectilinear thrust capabilities of the subject invention by advancing, ejecting and forming the surgical staples stored in the cartridge. During the staple forming operation, the clutch assembly operates as described hereinbefore.

At the conclusion of the staple forming operation, the compression tension provided by the return sring 32' causes the rocker arm 40' to pivot in a counter-clockwise direction about pivot pin 41' and thereby draw the thrust bar 30 to its ready position. The movement of the rocker arm 40' causes the trigger 28' to return to its ready position via the movement of link pair 45'. The explanation of the mechanical advantage obtained by the linkage arrangement of this embodiment is the same as that previously described for the first embodiment.

The nose portion 20' is fully rotatable within the housing 12'. A rotation of the nose portion also rotates the thrust bar 30 and the staple-carrying cartridge 26. Thus, the staple cartridge may be rotated into any position, as determined by the surgeon, during the use of the stapling instrument.

A third embodiment of the subject invention will now be described with reference to FIGS. 26–38. This embodiment operates in a manner similar to that of the first and second embodiments; the major difference being structural. Since this embodiment is for a disposable stapling instrument, all of the instrument components, unless specified otherwise, are made from a suitable plastic, such as ABS resin.

As best seen in FIGS. 26, 30, 32 and 35, the stapler, shown generally at 200, comprises a hollow body or housing 202 which defines a cartridge-receiving portion 204 and a drive mechanism-receiving portion 206. The generally rectangular hollow body 202 is defined by a top wall 208, a bottom wall 210 and a pair of side walls, 212 and 213. At the front of the body 202 is an opening 214 for receiving a staple-carrying cartridge 26. At the rear of the body is an opening 216 for receiving a portion of the staple-driving means. An outer handle 218 is pivotally mounted to a vertically extending post 220 which is offset from the front end of the side wall 212. An inner handle 222 is pivotally mounted to a post 224 which is offset from the front end of the side wall 213. The outer handle 218 contains a hand-engaging portion 219 and a force-transmitting portion 221. The inner handle 222 also contains a hand-engaging portion 235 and a force-transmitting portion 237.

A drive means comprising a stainless steel thrust bar 230, containing a tab 233, and a linkage arrangement, generally designated as 240, responds to a manipulative force supplied to the handles by the surgeon in order to advance, eject and form, by mechanical means only, the surgical staples carried in the staple-carrying cartridge 26 (see FIG. 1a). Pivoting the handles, 218 and 222, causes the thrust bar 230 to drive the pusher 27 of the staple-carrying cartridge 26 forward to advance, eject and form the staples. At the conclusion of a staple-forming operation, a stainless steel return spring 232, cooperating with the handles and the thrust bar, returns the thrust bar and the handles to their respective ready positions for the next stapling operation (see FIG. 32).

The specific structure of this embodiment will now be described in greater detail with reference to FIGS. 30 through 32 and 35. Inside of the body, there is provided a slot 268 defined by generally planar surface 270 and side walls 271–272. The substantially planar thrust bar is adapted for movement longitudinally within the slot 268. The stainless steel thrust bar comprises an elongated body 250, an elongated neck 252 depending from the body, and a head 254 depending from the neck. Downwardly depending from the front portion of the head is a tab 233, the configuration of which is chosen to mate with a complementary recess in the pusher 27 of the staple-carrying cartridge 26. A slot 261 for the head 254 is provided with the housing 202 and is defined by the surface 262 and the two side walls, 264 (see FIG. 35). At the rearward portion of the thrust bar body 250, there is an aperture 311 for receiving a stainless steel hinge pin 267.

With reference now to FIGS. 30–32, 34 and 35, the inner handle 222 is generally hollow; the hollow space being defined by the upper and lower surfaces, 280 and 281, respectively, and the wall 283. The distance between the two walls, 280 and 281, is chosen to receive the housing 202 within the handle when the inner handle 222 is pivoted about the post 224. The outer handle 218 contains a hollow portion defined by the upper and lower surfaces, 290 and 291, respectively, and the wall 292. The distance between the upper and lower surfaces 290 and 291 is chosen to receive both the housing 202 and the inner handle 222 when the outer handle 218 is pivoted about the post 220. Bulges 282, as shown in FIG. 29, are provided on both of the handles as a means of alerting the surgeon to the proper orientation of the stapler.

An inner link 245 is pivotally mounted at the force-transmitting portion 237 of the inner handle 222 by a pair of projections 286. An outer link 246 is pivotally mounted at the force-transmitting portion 221 of the outer handle 218 by a pair of projections 288. It should be noted that the links 245 and 246 may be interchangeably mounted to the handles 218 and 222.

Contained within the housing 202, as shown in FIGS. 31, 35 and 36, is a longitudinally extending cylindrical bore 300 for receving the spring 232. A connecting pin 302 comprises a collar 304, a finger 306 depending from the collar, and a tongue 308 depending from the opposite side of the collar. The generally cylindrical finger 306 is of a particular diameter so as to be slidably received within the return spring 232. The collar 304 provides a shoulder surface for supporting a free end of the spring 232. The other end of the spring is supported in the bore 300 by the bore wall 310. As best illustrated in FIG. 37, apertures 311-314 of the thrust bar, the tongue, the outer link and the inner link, respectively, are brought into registry to receive the hinge pin 267.

The thrust bar will now be described with reference to FIGS. 32 and 33. As stated before, the thrust bar 230, which is an elongated substantially planar member containing an upper surface 320 and a lower surface 322, comprises a longitudinally extending body portion 250, a longitudinally extending neck 252 depending from the body portion, and a head section 254 depending from the neck portion. The transverse width of the head section 254 is chosen to allow longitudinal movement within the guideway 261 provided within the housing 202. The width of the narrow midsection 252 is chosen to allow free movement between the cartridge tabs 78. The dimension of body section 250 is chosen to allow free movement within the guideway 268 provided within the housing 202.

Mounted on the body 250 of the thrust bar is a clutch assembly, noted generally as 330. Clutch assembly 330 comprises a stainless steel pawl 332 and a stainless steel bias spring 334. The stainless steel thrust bar 230 contains a depression 331 to create, below the bottom surface of the thrust bar, an open area 336 for receiving the pawl 332. Three downwardly projecting fingers 345-347 are provided to receive the pawl. One end of the bias spring 334 is held in place by two downwardly extending projections 340. The length of the bias spring 334 passes through two thrust bar apertures 341-342. The bias spring is held in place in aperture 342 by spring finger 344. The bias spring 334 is used to maintain the pawl in a generally transverse position with respect to the axis of the thrust bar 230. As can be seen, the longitudinal dimension of the pawl is slightly greater than the distance from finger 346 to the edge 348 of the thrust bar 230.

The operation of the clutch assembly will now be described with reference to FIG. 32. Except as noted below, the thrust bar 230 and the clutch assembly 330 operate in a manner similar to the thrust bar 30 and clutch assembly 114 previously described with reference to stapler 10 and FIGS. 6a through 6d. Within the drive mechanism-receiving portion 206, side wall 212 has two cutouts 350 and 351. These cutouts allow the pawl 332 to be in a generally transverse position with respect to the thrust bar. The portion of side wall 212 remaining between the two cutouts, 350 and 351, defines a surface 352. The length of the surface 352, defined between the cutouts 350 and 351, is slightly shorter than the distance travelled by the thrust bar 230 during a staple forming operation. When the thrust bar 230 is in the return position, the pawl is located to the right of the surface 352 within the cutout 351. When a stapling operation begins, the thrust bar is moved to the left and the pawl encounters the surface 352. The tip of the pawl 332 is caused to move in a direction opposite to that travelled by the thrust bar. If movement of the thrust bar is interrupted before the completion of the stapling operating, the pawl will be located between the surface 352 and the finger 346. The return spring 232 provides tension to try and return the thrust bar to is ready position. The tip and the rounded portion of the pawl are wedged between the surface 352 and the finger 346 to prevent this action from taking place. Thus, a complete stapling cycle must be completed before the thrust bar can be returned to its ready position.

Once the staple-forming operation has been completed, the pawl is located to the left of the surface 352 in the cutout area 350. At the completion of the stapling cycle, the pawl 332, under the urging of the bias spring 334, is in a generally transverse position with respect to the longitudinal axis of the thrust bar 230. The return spring 232 now causes the thrust bar to return to its home position. While this takes place, the tip of the pawl is deflected by the surface 352 in a direction opposite to that travelled by the thrust bar. If a surgeon attempts to initiate a stapling operation during the return trip of the thrust bar, the pawl restricts the movement of the thrust bar. When tension on the handles is removed, the thrust bar continues its return trip to the ready position. Thus, the clutch assembly acts to prevent the occurrence of staple jams in the staple-carrying cartridge 26.

The operation of the stapling instrument will now be described with reference to FIGS. 26, 32 and 35. The disposable plastic stapling instrument comes with the staple-carrying cartridge already in place. The front portion 204 of the housing 202 is adapted to permanently hold the staple-carrying cartridge 26. As best seen in FIGS. 31 and 35, a stop provided by transverse wall 360 limits the extent to which the cartridge may be inserted into the housing. The staple-carrying cartridge 26 is held in place within the housing by upwardly extending ledges, 361 and 362, and surface 364, containing a number of longitudinal and transverse sections. The staple-carrying cartridge 26 (see FIG. 1a) has a pair of upwardly extending, spaced tabs 78 at its rear end. The spacing between tabs 78 is sufficient to allow neck portion 252 of the thrust bar 230 to freely slide therebetween, and tabs 78 are dimensioned so as to fit up against the wall 366 near the rearwardmost end of the surface 364. An upwardly projecting key 368 (FIGS. 28 and 30), contained on ledge 361, is received in a mating recess in the staple-carrying cartridge 26. When tabs 78 are properly positioned and key 368 is mated with the recess, the staple-carrying cartridge 26 cannot be pulled out of housing 202 of stapler, and cartridge 26 is fixed against forward movement during the stapling operation. The slot 261 is provided to slidably receive the head 254 of the thrust bar 230. This slot maintains the thrust bar 230 in intimate contact with the top surface of the staple-carrying cartridge 26.

For use, the surgeon grasps the instrument by placing the thumb along the side of one of the handles and the fingers along the side of the other handle. The fingers are then moved in a manner similar to the forming of a fist in order to draw the inner and outer handles, 222 and 219, respectively, toward each other. Under the force applied by the surgeon, the inner handle 222 pivots in a counter-clockwise direction about post 224, and the outer handle 218 pivots in a clockwise direction about post 220. The arcuate movement of each handle is transferred to each link. The inner link 245 pivots in a counter-clockwise direction about the projections 286, and the outer link 246 pivots in a clockwise direction about the projections 288. In this way, the manipulative force applied by the surgeon to the handles is transferred to the hinge pin 267 via the inner link 245 and the outer link 246. In response to force supplied to the hinge pin, the thrust bar 230 moves, within the slot 268, in a direction generally designated by the arrow. In like manner, the connector pin 302 is caused to move in the same direction as the thrust bar, thus compressing the return spring 232. The compression of the return spring provides a return tension on the connector pin. The tab 233 of the thrust bar causes the pusher blade 27 of the staple cartridge 26 to move to accomplish the stapling operation. The mechanism within the staple-carrying cartridge 26 responds to the rectilinear thrust capabilities of the subject invention by advancing, ejecting and forming the surgical staples stored in the cartridge. During the stapling cycle, the clutch assembly operates as described hereinbefore.

At the conclusion of the stapling cycle, the compression tension provided by the return spring 232 causes the handles, 218 and 222, and the thrust bar 230 to return to their initial positions. The thrust-bar-head guideway 261 restricts the return motion to a defined distance.

In the third embodiment, explanation of the toggle linkage is made with reference to FIGS. 32 and 35. In this case the mechanism employs two symetric mirror image toggle systems. The one system is composed of the outer handle 218 which pivots about center 220 to displace link 246 and thrust bar 230, so that the center 267 moves to approach the line connecting centers 220 and 288. As center 267 approaches this line, the mechanical advantage of this toggle system again approaches infinity. The inner handle 222 and inner link 245 perform exactly the same motions and function in mirror image. The sum of the forces generated by each toggle system is available to drive the thrust bar 230 with an increasingly large mechanical advantage as the pusher stroke progresses. Again this is desirable because the most work is done at the last part of the stroke when the staple is formed.

Above there has been described specific embodiments of the present invention. It should be noted, however, that the above description was given for illustrative purposes only and that many alterations and modifications may be practiced by those skilled in the art without departing from the spirit or the scope of the present invention. It is the intent therefore that the present invention not be limited to the above but be limited only as defined in the appended claims.

I claim:

1. A manually powered surgical stapling instrument for applying sterilized staples to the disunited skin or fascia of a patient for effecting a joining of the skin or fascia, the instrument adapted to associate with a staple-carrying cartridge having anvil means at one end thereof and adapted to house a plurality of staples therein, a pusher element slidably mounted therein for advancing said staples in said cartridge, for ejecting said staples from said cartridge and for forming said staples around said anvil means, said surgical stapling instrument comprising:

a main body portion;
   means for mounting said staple-carrying cartridge on said main body portion;
   a thrust bar adapted to be operatively associated with said pusher element and slidably mounted in said main body portion for reciprocative movement in a forward direction and a return direction between an initial position and a final position, said initial position being the position of said thrust bar before a staple has been advanced, said final position being the position of said thrust bar after a staple has been formed;
   a pawl;
   pawl-deflecting means for deflecting said pawl during movement of said thrust bar;
   pawl-mounting means including a pawl-contacting member for contacting a peripheral portion of said pawl, said pawl-mounting means for mounting said pawl on said thrust bar to permit deflection of said pawl by said pawl-deflecting means and movement of said thrust bar in said forward direction and said return direction between said initial and final positions, and for wedging said pawl between said pawl-deflecting means and said pawl-contacting member to prevent said thrust bar from returning to said initial position until said thrust bar has reached said final position during said forward movement of said thrust bar and to prevent said thrust bar from advancing to said final position until said thrust bar has returned to said initial position during said return movement of said thrust bar;
   handle means for receiving a manually applied force; and
   linkage means for transmitting said manually applied force to said thrust bar to advance said thrust bar and thereby advance, eject and form said staples.

2. The instrument according to claim 1, wherein said handle means comprises a handle pivotably mounted to said main body portion, said handle having a lower hand-engaging portion and an upper force-transmitting portion associated with said thrust bar.

3. The instrument according to claim 2, wherein said linkage means comprises:
   a rocker arm pivotally mounted in said main body portion and associated with said thrust bar; and
   link means, associated with said rocker arm and said upper force-transmitting portion for transmitting said manually applied force to said thrust bar.

4. The instrument according to claim 1, wherein said handle means comprises a first handle pivotally mounted to said main body portion and a second handle pivotally mounted to said main body portion, each handle having a hand-engaging portion and a force-transmitting portion associated with said thrust bar.

5. The instrument according to claim 4, wherein said linkage means comprises a first link pivotally mounted to said force-transmitting portion of said first handle, and a second link pivotally mounted to said force-transmitting portion of said second handle, said first and second links cooperatively associated with said thrust bar for transmitting said manually applied force to said thrust bar.

6. The instrument according to claim 1, further comprising a nose portion rotatably mounted in said main body portion and means for mounting said staple-carrying cartridge in said nose portion so that said cartridge is rotatable therewith, said thrust bar being housed in said nose portion and rotatable therewith.

7. The instrument according to claim 1, wherein said pawl is mounted on said thrust bar.

8. A manually powered surgical stapling instrument for applying sterilized staples to the disunited skin or fascia of a patient for effecting a joining of the skin or fascia, said instrument comprising:
a staple-carrying cartridge having anvil means at one end thereof and adapted to house a plurality of said staples therein, and a pusher element slidably mounted therein for advancing said staples in said cartridge, for ejecting said staples from said cartridge and for forming said staples around said anvil means;
a main body portion;
means for mounting said staple-carrying cartridge on said main body portion;
a thrust bar operatively associated with said pusher element and slidably mounted in said main body portion for reciprocative movement in a forward direction and a return direction between an initial position and a final position, said initial position being the position of said thrust bar before a staple has been advanced, said final position being the position of said thrust bar after a staple has been formed;
a pawl;
pawl-deflecting means for deflecting said pawl during movement of said thrust bar;
pawl-mounting means including a pawl-contacting member for contacting a peripheral portion of said pawl, said pawl-mounting means for mounting said pawl on said thrust bar to permit deflection of said pawl by said pawl-deflecting means and movement of said thrust bar in said forward direction and said return direction between said initial and final positions, and for wedging said pawl between said pawl-deflecting means and said pawl-contacting member to prevent said thrust bar from returning to said initial position until said thrust bar has reached said final position during said forward movement of said thrust bar and to prevent said thrust bar from advancing to said final position until said thrust bar has returned to said initial position during said return movement of said thrust bar;
handle means for receiving a manually applied force; and
linkage means for directly transmitting said manually applied force to said thrust bar to advance said thrust bar and thereby advance, eject and form said staples.

9. The instrument according to claim 8, wherein said handle means comprises a handle pivotably mounted to said main body portion, said handle having a lower hand-engaging portion and an upper force-transmitting portion associated with said thrust bar.

10. The instrument according to claim 9, wherein said linkage means comprises:
a rocker arm pivotally mounted in said main body portion and associated with said thrust bar; and
link means, associated with said rocker arm and said upper force-transmitting portion for transmitting said manually applied force to said thrust bar.

11. The instrument according to claim 8, wherein said handle means comprises a first handle pivotally mounted to said main body portion and a second handle pivotally mounted to said main body portion, each handle having a hand-engaging portion and a force-transmitting portion associated with said thrust bar.

12. The instrument according to claim 11, wherein said linkage means comprises a first link pivotally mounted to said force-transmitting portion of said first handle, and a second link pivotally mounted to said force-transmitting portion of said second handle, said first and second links cooperatively associated with said thrust bar for transmitting said manually applied force to said thrust bar.

13. The instrument according to claim 8, further comprising a nose portion rotatably mounted in said main body portion and means for mounting said staple-carrying cartridge in said nose portion so that said cartridge is rotatable therewith, said thrust bar being housed in said nose portion and rotatable therewith.

14. The instrument according to claim 8, wherein said pawl is mounted on said thrust bar.

15. The instrument according to claim 1, wherein said pawl-contacting member is defined by said thrust bar.

16. The instrument according to claim 1, wherein said pawl-contacting member is defined by said main body portion.

17. The instrument according to claim 6, wherein said pawl-contacting member is defined by said nose portion.

18. The instrument according to claim 1, wherein said pawl-mounting means includes means for urging said peripheral portion of said pawl against said pawl-contacting member.

19. The instrument according to claim 8, wherein said pawl-contacting member is defined by said thrust bar.

20. The instrument according to claim 8, wherein said pawl-contacting member is defined by said main body portion.

21. The instrument according to claim 13, wherein said pawl-contacting member is defined by said nose portion.

22. The instrument according to claim 8, wherein said pawl-mounting means includes means for urging said peripheral portion of said pawl against said pawl-contacting member.

23. A manually powered surgical stapling instrument for applying sterilized staples to the disunited skin or fascia of a patient for effecting a joining of the skin or fascia, the instrument adapted to associate with a staple-carrying cartridge having anvil means at one end thereof and adapted to house a plurality of staples therein, and a pusher element slidably mounted therein for advancing said staples in said cartridge, for ejecting said staples from said cartridge, and for forming said staples around said anvil means, said surgical stapling instrument comprising:

a main body portion;

a nose portion rotatably mounted in said main body portion;

means for mounting said staple-carrying cartridge in said nose portion so that said staple-carrying cartridge is rotatable therewith;

a thrust bar adapted to be operatively associated with said pusher element and slidably mounted in said nose portion so that said thrust bar is rotatable therewith, said thrust bar being slidably mounted for reciprocative movement in a forward direction and a return direction between an initial position and a final position, said initial position being the position of said thrust bar before a staple has been advanced, said final position being the position of said thrust bar after a staple has been formed;

clutch means mounted in said nose portion so that said clutch means is rotatable therewith, said clutch means for accomplishing the dual purpose of preventing said thrust bar from returning to said initial position until said thrust bar has reached said final position during said forward movement of said thrust bar, and of preventing said thrust bar from advancing to said final position until said thrust bar has returned to said initial position during said return movement of said thrust bar;

handle means for receiving a manually applied force; and linkage means for transmitting said manually applied force to said thrust bar to advance said thrust bar and thereby advance, eject and form said staples.

24. The instrument according to claim 23, wherein said handle means comprises a handle pivotably mounted to said main body portion, said handle having a lower hand-engaging portion and an upper force-transmitting portion associated with said thrust bar.

25. The instrument according to claim 24, wherein said linkage means comprises:

a rocker arm pivotally mounted in said main body portion and associated with said thrust bar; and link means, associated with said rocker arm and said upper force-transmitting portion for transmitting said manually applied force to said thrust bar.

26. The instrument according to claim 23, wherein said handle means comprises a first handle pivotally mounted to said main body portion and a second handle pivotally mounted to said main body portion, each handle having a hand-engaging portion and a force-transmitting portion associated with said thrust bar.

27. The instrument according to claim 26, wherein said linkage means comprises a first link pivotally mounted to said force-transmitting portion of said first handle, and a second link pivotally mounted to said force-transmitting portion of said second handle, said first and second links cooperatively associated with said thrust bar for transmitting said manually applied force to said thrust bar.

28. The instrument according to claim 23, wherein said clutch means is mounted on said thrust bar.

29. A manually powered surgical stapling instrument for applying sterilized staples to the disunited skin or fascia of a patient for effecting a joining of the skin or fascia, said instrument comprising:

a staple-carrying cartridge having anvil means at one end thereof and adapted to house a plurality of said staples therein, and a pusher element slidably mounted therein for advancing said staples in said cartridge, for ejecting said staples from said cartridge and for forming said staples around said anvil means;

a main body portion;

a nose portion rotatably mounted in said main body portion;

means for mounting said staple-carrying cartridge in said nose portion so that said staple-carrying cartridge is rotatable therewith;

a thrust bar operatively associated with said pusher element and slidably mounted in said nose portion so that said thrust bar is rotatable therewith, said thrust bar being slidably mounted for reciprocative movement in a forward direction and a return direction between an initial position and a final position, said initial position being the position of said thrust bar before a staple has been advanced, said final position being the position of said thrust bar after a staple has been formed;

clutch means mounted in said nose portion so that said clutch means is rotatable therewith, said clutch means accomplishing the dual purpose of preventing said thrust bar from returning to said initial position until said thrust bar has reached said final position during said forward movement of said thrust bar, and of preventing said thrust bar from advancing to said final position until said thrust bar has returned to said initial position during said return movement of said thrust bar;

handle means for receiving a manually applied force; and linkage means for directly transmitting said manually applied force to said thrust bar to advance said thrust bar and thereby advance, eject and form said staples.

30. The instrument according to claim 29, wherein said handle means comprises a handle pivotably mounted to said main body portion, said handle having a lower hand-engaging portion and an upper force-transmitting portion associated with said thrust bar.

31. The instrument according to claim 30, wherein said linkage means comprises:

a rocker arm pivotally mounted in said main body portion and associated with said thrust bar; and link means, associated with said rocker arm and said upper force-transmitting portion for transmitting said manually applied force to said thrust bar.

32. The instrument according to claim 29, wherein said handle means comprises a first handle pivotally mounted to main body portion and a second handle pivotally mounted to said main body portion, each handle having a hand-engaging portion and a force-transmitting portion associated with said thrust bar.

33. The instrument according to claim 32, wherein said linkage means comprises a first link pivotally mounted to said force-transmitting portion of said first handle, and a second link pivotally mounted to said force-transmitting portion of said second handle, said first and second links cooperatively associated with said thrust bar for transmitting said manually applied force to said thrust bar.

34. The instrument according to claim 29, wherein said clutch means is mounted on said thrust bar.

35. A manually powered surgical stapling instrument for applying sterilized staples to the disunited skin or fascia of a patient for effecting a joining of the skin or fascia, the instrument adapted to associate with a staple-carrying cartridge having anvil means at one end thereof and adapted to house a plurality of staples therein, and a pusher element slidably mounted therein for advancing said staples in said cartridge, for ejecting said staples from said cartridge and for forming said staples around said anvil means, said surgical stapling instrument comprising:

a main body portion;

means for mounting said staple-carrying cartridge on said main body portion;

a thrust bar adapted to be operatively associated with said pusher element and slidably mounted in said main body portion for reciprocative movement in a forward direction and a return direction between an initial position and a final position, said initial position being the position of said thrust bar before a staple has been advanced, said final position being the position of said thrust bar after a staple has been formed;

handle means pivotally mounted to said main body portion, said handle means having an upper force-transmitting portion, and a lower hand-engaging portion for receiving a manually applied force;

a rocker arm pivotally mounted in said main body portion and associated with said thrust bar; and link means, associated with said rocker arm and said upper force-transmitting portion for transmitting said manually applied force to said thrust bar.

36. The instrument according to claim 35, further comprising a nose portion rotatably mounted in said main body portion and means for mounting said staple-carrying cartridge in said nose portion so that said cartridge is rotatable therewith, said thrust bar being housed in said nose portion and rotatable therewith.

37. The instrument according to claim 35, further comprising clutch means for preventing said thrust bar from returning to said initial position until said thrust bar has reached said final position during said forward movement of said thrust bar, and for preventing said thrust bar from advancing to said final position until said thrust bar has returned to said initial position during said return movement of said thrust bar.

38. The instrument according to claim 37, wherein said clutch means is mounted on said thrust bar.

39. A manually powered surgical stapling instrument for applying sterilized staples to the disunited skin or fascia of a patient for effecting a joining of the skin or fascia, said instrument comprising:

a staple-carrying cartridge having anvil means at one end thereof and adapted to house a plurality of said staples therein, and a pusher element slidably mounted therein for advancing said staples in said cartridge, for ejecting said staples from said cartridge and for forming said staples around said anvil means;

a main body portion;

means for mounting said staple-carrying cartridge on said main body portion;

a thrust bar operatively associated with said pusher element and slidably mounted in said main body portion for reciprocative movement in a forward direction and a return direction between an initial position and a final position, said initial position being the position of said thrust bar before a staple has been advanced, said final position being the position of said thrust bar after a staple has been formed;

handle means pivotally mounted to said main body portion, said handle means having an upper force-transmitting portion, and a lower hand-engaging portion for receiving a manually applied force;

a rocker arm pivotally mounted in said main body portion and associated with said thrust bar; and link means, associated with said rocker arm and said upper force-transmitting portion for transmitting said manually applied force to said thrust bar.

40. The instrument according to claim 39, further comprising a nose portion rotatably mounted in said main body portion and means for mounting said staple-carrying cartridge in said nose portion so that said cartridge is rotatable therewith, said thrust bar being housed in said nose portion and rotatable therewith.

41. The instrument according to claim 39, further comprising clutch means for preventing said thrust bar from returning to said initial position until said thrust bar has reached said final position during said forward movement of said thrust bar and for preventing said thrust bar from advancing to said final position until said thrust bar has returned to said initial position during said return movement of said thrust bar.

42. The instrument according to claim 41, wherein said clutch means is mounted on said thrust bar.

43. A manually powered surgical stapling instrument for applying sterilized staples to the disunited skin or fascia of a patient for effecting a joining of the skin or fascia, the instrument adapted to associate with a staple-carrying cartridge which has an anvil means at one end thereof and is adapted to house a plurality of staples therein, and a pusher element slidably mounted in said cartridge for advancing said staples in said cartridge, for ejecting said staples from said cartridge and for forming said staples around said anvil means, said surgical stapling instrument comprising:

a main body portion;

means for mounting said staple-carrying cartridge on said main body portion;

a thrust bar adapted to be operatively associated with said pusher element and slidably mounted in said main body portion for reciprocative movement in a forward direction and a return direction between an initial position and a final position, said initial position being the position of said thrust bar before a staple has been advanced, said final position being the position of said thrust bar after a staple has been formed;

a first handle pivotally mounted to said main body portion and a second handle pivotally mounted to said main body portion, each handle having a hand-engaging portion for receiving a manually applied force, and a force-transmitting portion; and linkage means operatively connected to said force-transmitting portions and said thrust bar for transmitting said manually applied force to said thrust bar to advance said thrust bar and thereby advance, eject and form said staples.

44. The instrument according to claim 43, wherein said linkage means comprises a first link pivotally mounted to said force-transmitting portion of said first handle, and a second link pivotally mounted to said force-transmitting portion of said second handle, said first and second links cooperatively associated with said thrust bar for transmitting said manually applied force to said thrust bar.

45. The instrument according to claim 43, further comprising a nose portion rotatably mounted in said main body portion and means for mounting said staple-carrying cartridge in said nose portion so that said cartridge is rotatable therewith, said thrust bar being housed in said nose portion and rotatable therewith.

46. The instrument according to claim 43, further comprising clutch means for preventing said thrust bar from returning to said initial position until said thrust bar has reached said final position during said forward movement of said thrust bar and for preventing said thrust bar from advancing to said final position until said thrust bar has returned to said initial position during said return movement of said thrust bar.

47. The instrument according to claim 46, wherein said clutch means is mounted on said thrust bar.

48. A manually powered surgical stapling instrument for applying sterilized staples to the disunited skin or fascia of a patient for effecting a joining of the skin or fascia, said instrument comprising:
- a staple-carrying cartridge having anvil means at one end thereof and adapted to house a plurality of said staples therein, and a pusher element slidably mounted therein for advancing said staples in said cartridge, for ejecting said staples from said cartridge and for forming said staples around said anvil means;
- a main body portion;
- means for mounting said staple-carrying cartridge on said main body portion;
- a thrust bar operatively associated with said pusher element and slidably mounted in said main body portion for reciprocative movement in a forward direction and a return direction between an initial position and a final position, said initial position being the position of said thrust bar before a staple has been advanced, said final position being the position of said thrust bar after a staple has been formed;
- a first handle pivotally mounted to said main body portion and a second handle pivotally mounted to said main body portion, each handle having a hand-engaging portion for receiving a manually applied force, and a force-transmitting portion; and
- linkage means operatively connected to said force-transmitting portions and said thrust bar for transmitting said manually applied force to said thrust bar to advance said thrust bar and thereby advance, eject and form said staples.

49. The instrument according to claim 48, wherein said linkage means comprises a first link pivotally mounted to said force-transmitting portion of said first handle, and a second link pivotally mounted to said force-transmitting portion of said second handle, said first and second links cooperatively associated with said thrust bar for transmitting said manually applied force to said thrust bar.

50. The instrument according to claim 48, further comprising a nose portion rotatably mounted in said main body portion and means for mounting said staple-carrying cartridge in said nose portion so that said cartridge is rotatable therewith, said thrust bar being housed in said nose portion and rotatable therewith.

51. The instrument according to claim 48, further comprising clutch means for preventing said thrust bar from returning to said initial position until said thrust bar has reached said final position during said forward movement of said thrust bar, and for preventing said thrust bar from advancing to said final position until said thrust bar has returned to said initial position during said return movement of said thrust bar.

52. The instrument according to claim 51, wherein said clutch means is mounted on said thrust bar.

* * * * *